US011875890B2

(12) United States Patent
Worrell

(10) Patent No.: US 11,875,890 B2
(45) Date of Patent: Jan. 16, 2024

(54) FITNESS AND NUTRITION MANAGEMENT SYSTEM

(71) Applicant: R.E.A.C.H. Fitness, LLC, Portland, OR (US)

(72) Inventor: Valerie Worrell, Portland, OR (US)

(73) Assignee: REACH FITNESS LLC, Portland, OR (US)

( * ) Notice: Subject to any disclaimer, the term of this patent is extended or adjusted under 35 U.S.C. 154(b) by 129 days.

(21) Appl. No.: 17/145,324

(22) Filed: Jan. 9, 2021

(65) Prior Publication Data

US 2022/0139524 A1    May 5, 2022

Related U.S. Application Data

(60) Provisional application No. 63/110,342, filed on Nov. 5, 2020.

(51) Int. Cl.
| G09B 19/00 | (2006.01) |
| G16H 20/60 | (2018.01) |
| G16H 20/30 | (2018.01) |
| G06F 3/04847 | (2022.01) |
| G06F 3/0482 | (2013.01) |

(52) U.S. Cl.
CPC ......... *G16H 20/60* (2018.01); *G09B 19/0092* (2013.01); *G16H 20/30* (2018.01); *G06F 3/0482* (2013.01); *G06F 3/04847* (2013.01); *G09B 19/003* (2013.01)

(58) Field of Classification Search
CPC ............................. G09B 19/0092; G16H 20/60
See application file for complete search history.

(56) References Cited

U.S. PATENT DOCUMENTS

| 7,914,419 B2 | 3/2011 | Karkanias et al. |
| 8,303,500 B2 | 11/2012 | Raheman |
| 9,171,482 B2 | 10/2015 | Carter et al. |

(Continued)

FOREIGN PATENT DOCUMENTS

| KR | 10-1586661 B1 | 1/2016 |
| WO | 2013009589 A1 | 1/2013 |

(Continued)

OTHER PUBLICATIONS

International Search Report for PCT Patent Application PCT/US21/57771, dated Mar. 17, 2022.

(Continued)

*Primary Examiner* — Peter R Egloff
(74) *Attorney, Agent, or Firm* — Daniel C. Housley; The IP Gnome, LLC

(57) ABSTRACT

A system is described. This system may include a processor, storage for a table of foods consumed by a user, and a presentation system. The table may associate a serving of a food with a number of coins. The presentation system may inform the user that the user has spent too many coins based at least in part on a total of the number of coins in the table exceeds a recommended number of coins for the user. The number of coins associated with the serving of the food may be calculated based at least in part on a first number of grams of carbohydrates in the serving of the food, a second number of grams of proteins in the serving of the food, and a third number of grams of fats in the serving of the food.

20 Claims, 21 Drawing Sheets

(56) References Cited

U.S. PATENT DOCUMENTS

| | | | |
|---|---|---|---|
| 9,468,807 B1 | 10/2016 | Krueger et al. | |
| 2003/0226695 A1* | 12/2003 | Mault | A61B 5/0002 |
| | | | 128/921 |
| 2006/0122468 A1* | 6/2006 | Tavor | G16H 20/60 |
| | | | 600/300 |
| 2006/0205564 A1 | 9/2006 | Peterson | |
| 2007/0059672 A1* | 3/2007 | Shaw | G09B 19/0092 |
| | | | 708/100 |
| 2011/0151414 A1* | 6/2011 | McCarthy | G09B 19/0092 |
| | | | 434/127 |
| 2013/0132319 A1* | 5/2013 | Landers | G06N 5/02 |
| | | | 706/46 |
| 2013/0158367 A1 | 6/2013 | Pacione et al. | |
| 2013/0280681 A1 | 10/2013 | Narayan et al. | |
| 2014/0088995 A1 | 3/2014 | Damani | |
| 2014/0156308 A1 | 6/2014 | Ohnemus et al. | |
| 2014/0234807 A1* | 8/2014 | Lundin | G16H 20/30 |
| | | | 434/127 |
| 2015/0235562 A1 | 8/2015 | Klein | |
| 2016/0035248 A1* | 2/2016 | Gibbs | G06T 7/60 |
| | | | 434/127 |
| 2016/0240100 A1 | 8/2016 | Rauhala et al. | |
| 2017/0018199 A1 | 1/2017 | Mrowka et al. | |
| 2017/0173390 A1 | 6/2017 | Quy | |
| 2017/0249445 A1* | 8/2017 | Devries | A61B 5/742 |
| 2017/0372017 A1 | 12/2017 | Steffen | |
| 2018/0137776 A1* | 5/2018 | Farrer | G09B 19/0092 |
| 2018/0233233 A1 | 8/2018 | Solari | |
| 2018/0329584 A1 | 11/2018 | Williams et al. | |
| 2019/0065694 A1* | 2/2019 | Latham | G16H 40/63 |
| 2019/0130787 A1* | 5/2019 | DiFruscio | G09B 19/0092 |
| 2019/0147763 A1 | 5/2019 | Nusbaum et al. | |
| 2019/0259489 A1* | 8/2019 | De Petris | G16H 40/67 |
| 2020/0215392 A1 | 7/2020 | Hoffman et al. | |
| 2020/0227156 A1 | 7/2020 | Mainardi et al. | |
| 2020/0234557 A1 | 7/2020 | Yuen et al. | |

FOREIGN PATENT DOCUMENTS

| | | |
|---|---|---|
| WO | 2016110804 A1 | 7/2016 |
| WO | 2019217005 A1 | 11/2019 |

OTHER PUBLICATIONS

Written Opinion for PCT Patent Application PCT/US21/57771, dated Mar. 17, 2022.

Bruno F. Tavare, Ivan Miguel Pires, Gonçalo Marques, Nuno M. Garcia, Eftim Zdravevski, Petre Lameski, Vladimir Trajkovik and Aleksandar Jevremovic; "Mobile Applications for Training Plan Using Android Devices: A Systematic Review and a Taxonomy Proposal"; Information, vol. 11, No. 7, Jul. 2020; Multidisciplinary Digital Publishing Institute (MPDI), Basel, Switzerland.

* cited by examiner

Fitness

Gender: ⊗ Male ○ Female

Height: 72 in

Weight: 202 lbs

Age: 47

Activity Level: Somewhat Active ▼

Estimated Daily Calorie Needs: 2519 calories
BMI Measurement: 27

| Under-weight | Normal | Over-weight | Obese |

Weekly Weight Loss Goal: 1 lbs

Twelve week weight goal: 190 lbs
Estimated daily calories to reach weight loss goal: 2019 calories

FIG. 4A

| Date | Food | Servings | Coins |
|---|---|---|---|
| 06/29/2020 | 1 Egg | 2 | 1 |
| 06/29/2020 | 2 Egg whites | 1 | 0 |
| 06/29/2020 | ½ cup cooked Oats | 1 | 1 |
| 06/29/2020 | ¾ cup plain Yogurt | 1 | 1 |
| 06/29/2020 | 1 cup Fruit (grapes, berries, etc.) | 1 | 1 |
| 06/29/2020 | 4 whole Walnuts | 1 | 1 |
| 06/29/2020 | 1 slice Bread (Whole Wheat) | 2 | 2 |
| 06/29/2020 | 3 oz. cooked skinless Poultry | 1 | 1 |
| 06/29/2020 | 2 tbsp. Avocado | 2 | 1 |
| 06/29/2020 | 1 cup Unsweetened Soy Milk | 1 | 1 |
| 06/29/2020 | 1 small Fruit | 1 | 1 |
| 06/29/2020 | 13 Almonds | 1 | 1 |
| ⋮ | ⋮ | ⋮ | ⋮ |

FIG. 5

| Food ← 515 | Coins ← 525 | Carbohydrates (grams) ← 615 | Proteins (grams) ← 620 | Fats (grams) ← 625 |
|---|---|---|---|---|
| 1 Egg | 1 | 0 | 1 | 1 |
| 2 Egg whites | 0 | 0 | 0 | 0 |
| ½ cup cooked Oats | 1 | 1 | 0 | 0 |
| ¾ cup plain Yogurt | 1 | 0 | 1 | 0 |
| 1 cup Fruit (grapes, berries, etc.) | 1 | 1 | 0 | 0 |
| 4 whole Walnuts | 1 | 0 | 0 | 1 |
| 1 slice Bread (Whole Wheat) | 1 | 1 | 0 | 0 |
| ... | ... | ... | ... | ... |

FIG. 6

FITNESS AND NUTRITION MANAGEMENT SYSTEM

RELATED APPLICATION DATA

This application claims the benefit of U.S. Provisional Patent Application Ser. No. 63/110,342, filed Nov. 5, 2020, which is incorporated by reference herein for all purposes.

FIELD

The invention relates to generally to fitness and nutrition, and more particularly to a system for managing fitness and nutrition using macronutrients

BACKGROUND

The modern lifestyle, particularly in the United States of America, is not a particularly healthy lifestyle. A sedentary lifestyle, coupled for easy access to fast food that is not particularly healthy, has led to a significant percentage of the population being considered obese.

Solutions to these problems include improved nutrition and increased exercise. May diet programs exist that attempt to address these solutions.

But most diet programs concentrate on counting calories. While calories provide a starting point for improving diet, calories are not a complete solution to the problem of an unhealthy diet.

In addition, diet programs tend to concentrate on exercise as an end to itself. A participant is expected to exercise simply because exercise is part of the program. For someone motivated to lose weight, counting calories and exercising because it is expected might be enough to improve his or her lifestyle. But for someone who is not motivated, exercising just for the sake of exercising is often insufficient motivation.

A need remains to improve how to manage fitness and nutrition.

BRIEF DESCRIPTION OF THE DRAWINGS

FIGS. 4A-4H show various screens of the application of FIG. 1, according to embodiments of the invention.

FIG. 5 shows a table that may be used in the application of FIG. 1 to track foods consumed by the user, according to embodiments of the invention.

FIG. 6 shows a table that may be used in the application of FIG. 1 to determine a number of coins associated with a serving of food, according to embodiments of the invention.

DETAILED DESCRIPTION

Reference will now be made in detail to embodiments of the invention, examples of which are illustrated in the accompanying drawings. In the following detailed description, numerous specific details are set forth to enable a thorough understanding of the invention. It should be understood, however, that persons having ordinary skill in the art may practice the invention without these specific details. In other instances, well-known methods, procedures, components, circuits, and networks have not been described in detail so as not to unnecessarily obscure aspects of the embodiments.

It will be understood that, although the terms first, second, etc. may be used herein to describe various elements, these elements should not be limited by these terms. These terms are only used to distinguish one element from another. For example, a first module could be termed a second module, and, similarly, a second module could be termed a first module, without departing from the scope of the invention.

The terminology used in the description of the invention herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The components and features of the drawings are not necessarily drawn to scale.

Figure 1:
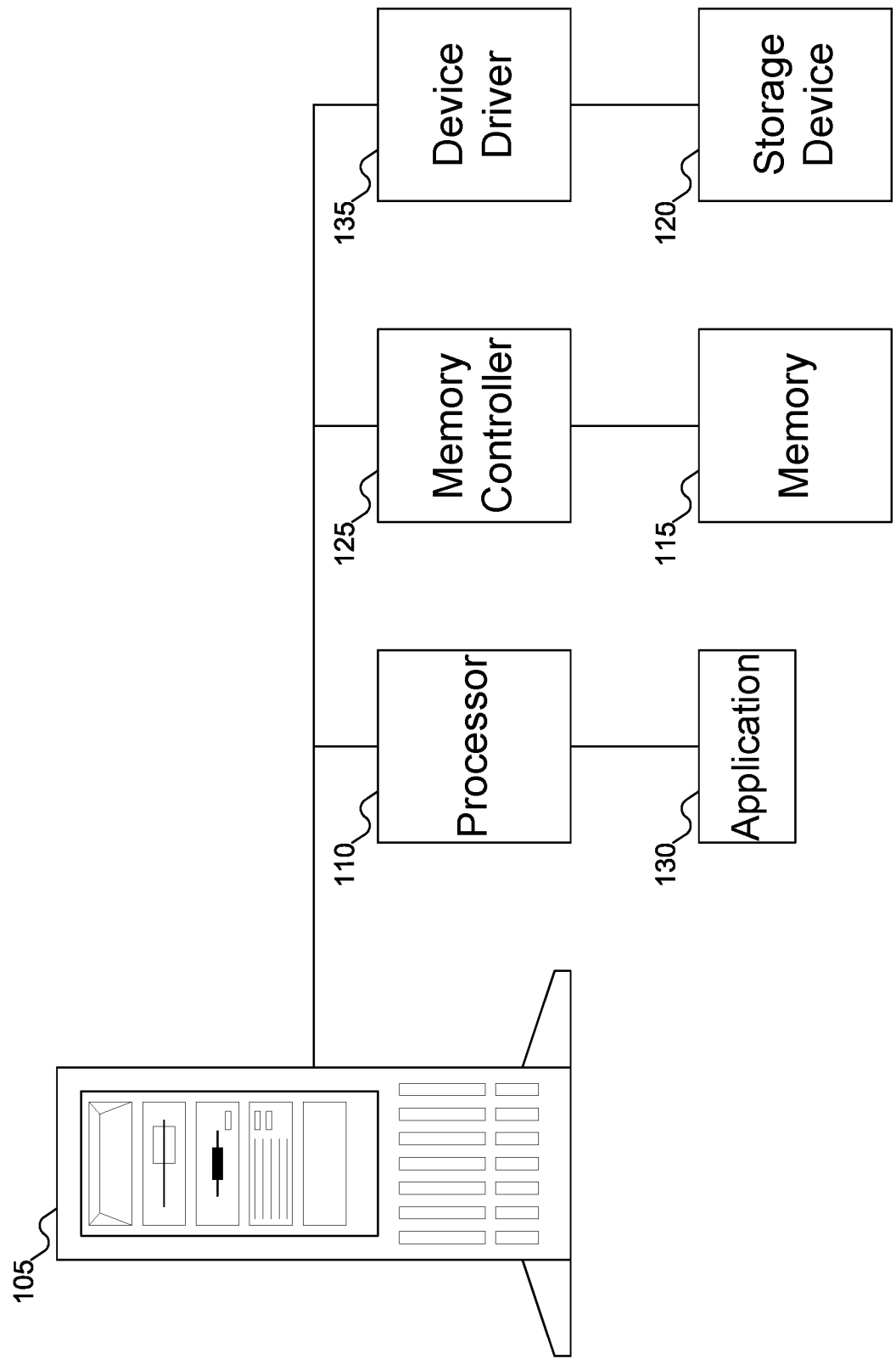
FIG. 1 shows a machine that may assist a user in managing fitness and nutrition, according to embodiments of the invention.

FIG. 1 shows a machine that may assist a user in managing fitness and nutrition, according to embodiments of the invention. In FIG. 1, machine 105 is shown. Machine 105 may include processor 110, memory 115, and storage device 120. Processor 110 may be any variety of processor. (Processor 110, along with the other components discussed below, are shown outside the machine for ease of illustration: embodiments of the invention may include these components within the machine.) While FIG. 1 shows a single processor 110, machine 105 may include any number of processors, each of which may be single core or multi-core processors, each of which may implement a Reduced Instruction Set Computer (RISC) architecture or a Complex Instruction Set Computer (CISC) architecture (among other possibilities), and may be mixed in any desired combination.

Processor 110 may be coupled to memory 115. Memory 115 may be any variety of memory, such as flash memory, Dynamic Random Access Memory (DRAM), Static Random Access Memory (SRAM), Persistent Random Access Memory, Ferroelectric Random Access Memory (FRAM), or Non-Volatile Random Access Memory (NVRAM), such as Magnetoresistive Random Access Memory (MRAM), etc. Memory 115 may also be any desired combination of different memory types, and may be managed by memory controller 125. Memory 115 may be used to store data that may be termed "short-term": that is, data not expected to be stored for extended periods of time. Examples of short-term data may include temporary files, data being used locally by applications (which may have been copied from other storage locations), and the like.

Processor 110 and memory 115 may also support an operating system under which various applications, such as application 130, which may be a fitness and nutrition management application, may be running. Application 130 may issue requests (which may also be termed commands) to read data from or write data to either memory 115 or storage device 120. Application 130 may also receive input from a user via a user interface. The user interface may include, among other possibilities, a keyboard, a mouse or other pointing device, or a microphone (which may be used to receive audio input, which may be processed using, for example, speech recognition software running on processor 110 or on a remote processor accessible from machine 105 via a network). Application 130 may also present information to the users via an output device. The output device may include, among other possibilities, a display or screen to present visual information and a speaker to present audio output.

In comparison with memory 115, storage device 120 may be used to store data that may be termed "long-term"; that is, data expected to be stored for extended periods of time. Storage device 120 may be accessed using device driver 135. While FIG. 1 uses the generic term "storage device", embodiments of the invention may include any storage device formats, examples of which may include hard disk drives and Solid State Drives (SSDs). Any reference to any such terms below should be understood to include alternative embodiments of the invention.

While FIG. 1 shows memory 115 and storage device 120 as separate elements, embodiments of the invention may use just one such element for both purposes. That is, either of memory 115 or storage device 120 may be used to store information that might otherwise be stored in the other element.

Machine 105 may also include hardware to support a network connection (not shown in FIG. 1). For example, machine 105 may communicate with a network, such as a Local Area Network (LAN), a Wide Area Network (WAN), a Metropolitan Area Network (MAN), or a global network, such as the Internet. In addition, machine 105 may communicate with or across multiple such networks. To communicate with such networks, machine 105 may include a wired network connection, such as an Ethernet port (which may be implemented as, for example, an RJ-45 connector) or a wireless network connection (which may be implemented as, for example, an antenna that may support any or all standards for wireless communication, such as 802.11a/b/g/n/ac/ax and/or Bluetooth® (Bluetooth is a trademark of Bluetooth SIG and its affiliates)).

While FIG. 1 shows machine 105 as a tower computer or a server, embodiments of the invention may include other implementations of machine 105. Machine 105 may be implemented as, for example, a desktop computer, a laptop, a mobile device, or a smartphone, among other possibilities.

Figure 2:
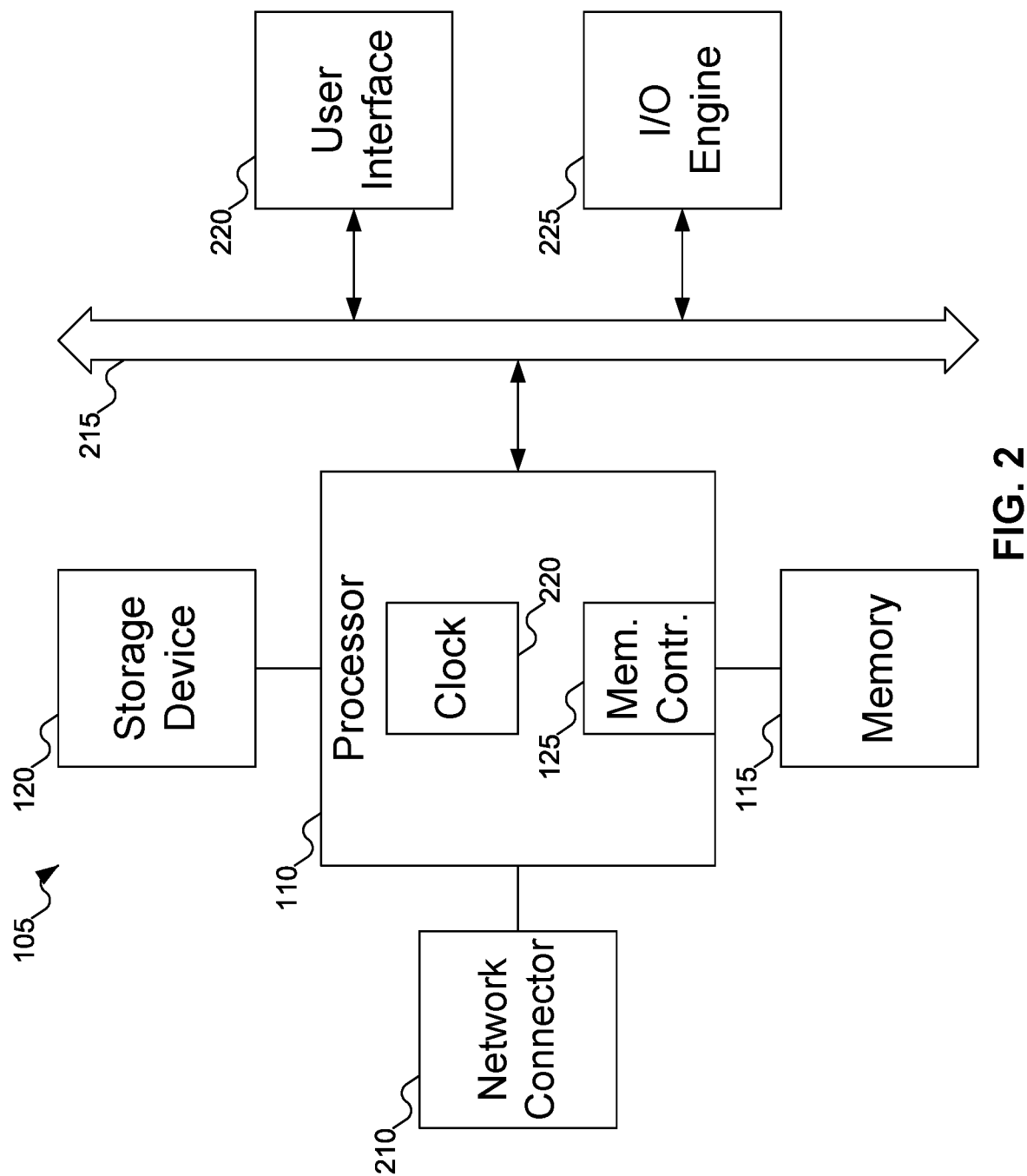
FIG. 2 shows additional details of the machine of FIG. 1, according to embodiments of the invention.

FIG. 2 shows details of machine 105 of FIG. 1, according to embodiments of the invention. In FIG. 2, typically, machine 105 includes one or more processors 110, which may include memory controllers 125 and clocks 205, which may be used to coordinate the operations of the components of the machine. Processors 110 may also be coupled to memories 115, which may include random access memory (RAM), read-only memory (ROM), or other state preserving media, as examples. Processors 110 may also be coupled to storage devices 120, and to network connector 210, which may be, for example, an Ethernet connector or a wireless connector. Processors 110 may also be connected to buses 215, to which may be attached user interfaces 220 and Input/Output (I/O) interface ports that may be managed using I/O engines 225, among other components.

Figure 3:
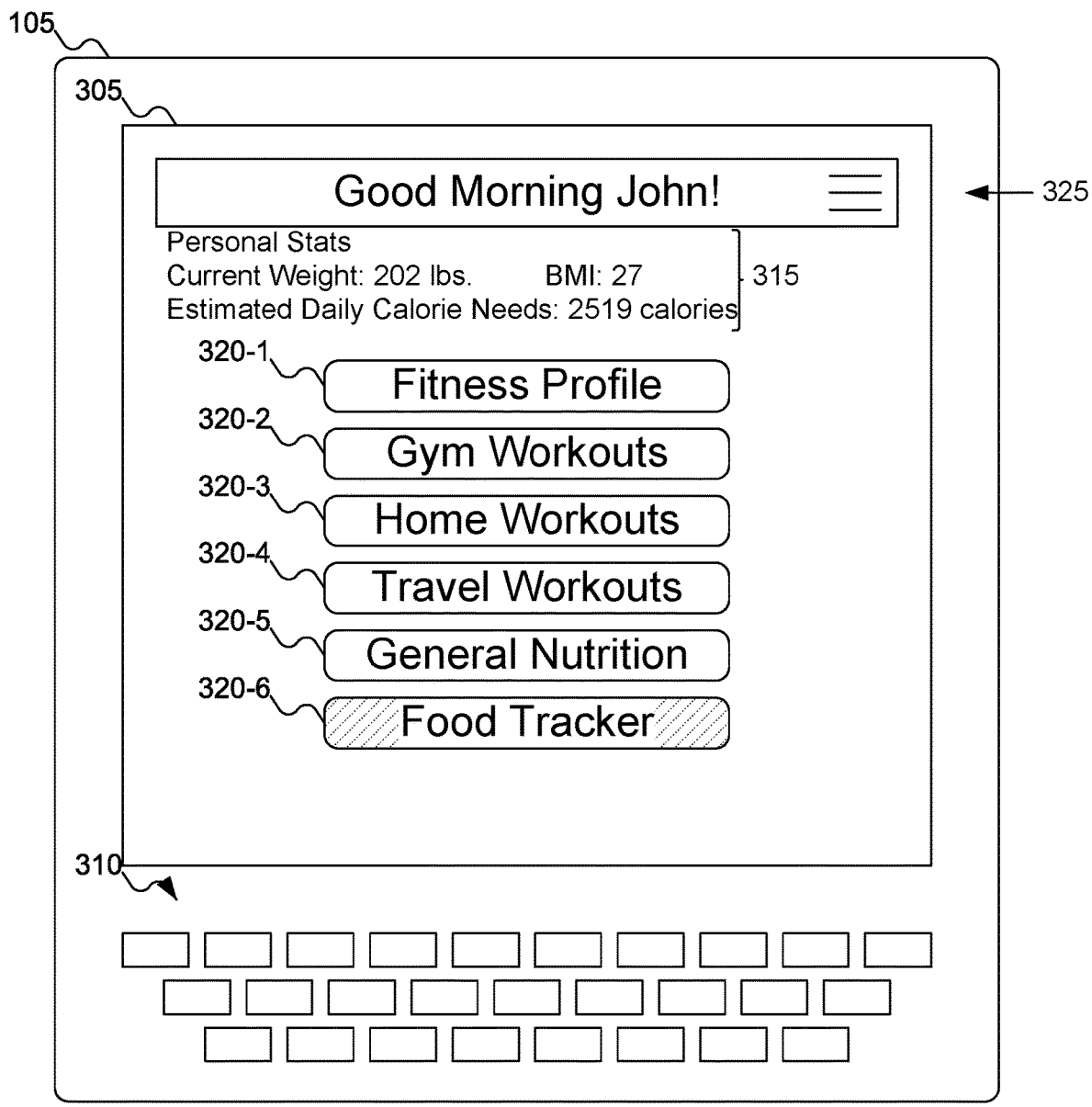
FIG. 3 shows the machine of FIG. 1 including an application to assist a user in managing fitness and nutrition, according to embodiments of the invention.

FIG. 3 shows machine 105 of FIG. 1 including application 130 of FIG. 1 to assist a user in managing fitness and nutrition, according to embodiments of the invention. In FIG. 3, machine 105 is shown as a mobile device or smartphone (and will be referred to hereafter as "smartphone"). Smartphone 105 may include screen 305 and user interface 310. Screen 305 may be used to present visual information to the user; user interface 310, shown as a keyboard, may be used to receive input from the user (and will be referred to hereafter as "keyboard"). Screen 305 is an example of a presentation system that may be used to present information the user: other presentation systems may include, for example, a speaker (for audio output), tactile interfaces, and the like. Presentation systems may also include combinations of such elements. While FIG. 3 shows keyboard 310 as being separate from screen 305, embodiments of the invention may include screen 305 as a touchscreen and presenting keyboard 310 within screen 310. Smartphone 105 may also include other elements not shown in FIG. 3, such as a speaker for audio output, mechanisms (such as buttons) to turn smartphone 105 on and off or to adjust the volume of the speaker, and so on.

Smartphone 105 is shown running application 130 of FIG. 1, which assists a user in managing fitness and nutrition. Screen 305 is shown presenting a start page, which may be displayed when application 130 of FIG. 1 first starts executing on processor 110 of FIG. 1. The start page may greet the user ("Good Morning, John", with the greeting modified for the appropriate time of day, which may be determined using a clock in smartphone 105).

The start page may include information 315 that may be of general interest to the user. Such information may include, for example, the user's personal statistics, such as their current weight and Body Mass Index (BMI) and their estimated daily calorie needs to maintain their current weight.

The start page also include buttons that may be pressed to jump to other pages in application 130 of FIG. 1. For example, button 320-1 may take the user to a page where the user may set up his or her fitness profile (shown in FIG. 4A below), button 320-2 may take the user to a page where the user may select workouts performed at a gym (shown in FIG. 4B below), button 320-3 may take the user to a page where the user may select workouts performed at home (shown in FIG. 4C below), button 320-4 may take the user to a page where the user may select workouts performed while traveling (shown in FIG. 4D below), button 320-5 may take the user to a page where the user may learn general information about nutrition (shown in FIG. 4E below), and button 320-6 may take the user to a page where the user may track the foods the user has consumed (shown in FIG. 4F below).

Note that button 320-6 is shown cross-hatched. This cross-hatching may be used to represent that button 320-6 is currently disabled. For example, certain features of application 130 of FIG. 1 may be disabled until the user activates them (for example, by purchasing a subscription to a more advanced service, or paying some fee). Rather than using cross-hatching, button 320-6 might be shaded or colored differently from buttons 320-1 through 320-5, to indicate that button 320-6 is current disabled (and application 130 of FIG. 1 may ignore any attempt by the user to press button 320-6). In the remainder of this document, no links, buttons, or other information is shown as disabled, but other links, buttons, or information may be disabled similarly to button 320-6, and indicated as disabled similarly as well.

The start page (and other pages as well) may also include "hamburger" 325—the three lines that may be used to open a menu with links to other pages within application 130 of FIG. 1. Hamburger 325 may include links to pages similar to those reached via buttons 320-1 through 320-6, and may also include links to other pages, such as pages including additional nutrition information, recipes that may be used, a shop where products, possibly related to fitness and nutrition, may be purchased, and information about application 130 of FIG. 1 producer and links to contact application 130 of FIG. 1 producer.

FIGS. 4A-4H show various screens of application 130 of FIG. 1, according to embodiments of the invention. Starting with FIG. 4A, screen 305 shows a page where the user may provide information about themselves. (Prior to this screen being displayed, application 130 of FIG. 1 may present a questionnaire to the user to confirm that the user is ready to engage in physical activity, inquiring about, for example, whether the user has a heart condition and should perform only exercised recommended by a doctor, whether the user feels any chest pain during physical activity (or chest pain when not engaged in physical activity), whether the user loses balance due to dizziness or loses consciousness, whether the user has a bone or joint problem that could be exacerbated by physical activity, whether a doctor has prescribed medication for a heart condition or for the user's blood pressure, and/or whether the user knows of any other reason not to engage in physical activity. If the user presents any reason not to engage in physical activity, the user may be referred to a doctor before proceeding.)

As shown in FIG. 4A, the user may specify whether the user is male or female, provide his or her height, weight, and age, and his or her activity level. These fields may be fields into which the user may type (or otherwise directly input) the appropriate values, or may be drop down lists from which the user may select the desired values. Activity levels may be categorized as, for example, sedentary (little or no exercise), somewhat active (light exercise or sports 1-3 days/week), active (moderate exercise or sports 3-5 days/week), or very active (moderate to vigorous exercise or sports 6-7 day/week). Using this information, application 130 of FIG. 1 may estimate the user's daily calorie needs to maintain their weight and the user's BMI.

BMI may be calculated using the equation shown in Equation (1), where W is the user's weight in pounds and H is the user's height in inches:

$$BMI = \left(\frac{W}{H^2}\right) \times 703 \quad \text{Equation (1)}$$

Thus, for the user whose personal information is shown in FIG. 4A, with a weight of 202 pounds and a height of 72 inches, the user's BMI is 27, which puts the user in the "overweight" category (the other categories being "underweight", "normal", and "obese"). The user's BMI (and its category) may also be shown graphically: the cross-hatching in FIG. 4A covers the "underweight" and "normal" categories completely, and partially covers the "overweight" category.

To calculate the user's estimated daily calorie needs, the user's Resting Energy Expenditure (REE) may be multiplied by a factor. The factor may be determined using the user's activity level, as shown in Table 1.

TABLE 1

| Activity Level | Factor |
| --- | --- |
| Sedentary | 1.200 |
| Somewhat Active | 1.375 |
| Active | 1.550 |
| Very Active | 1.725 |

The REE may be calculated using the equations shown in Equation (2a) or Equation (2b), depending on whether the user is a man (Equation (2a)) or a woman (Equation (2b)). In both Equation (2a) and Equation (2b), W is the user's weight in pounds, H is the user's height in inches, and A is the user's age in years:

$$REE = \left(9.99 \times \left(\frac{W}{2.205}\right)\right) + (6.25 \times (H \times 2.54)) - (4.92 \times A) + 5 \quad \text{Equation (2a)}$$

$$REE = \left(9.99 \times \left(\frac{W}{2.205}\right)\right) + (6.25 \times (H \times 2.54)) - (4.92 \times A) - 161 \quad \text{Equation (2b)}$$

Note that the difference between the two equations is the additive factor at the end.

Once the REE and the factor are known, the user's estimated daily calorie needs may be calculated as shown in Equation (3):

$$\text{Estimated Daily Calorie Needs} = REE \times Factor \quad \text{Equation (3)}$$

The user may also specify a desired weekly weight loss goal. This field may be a field into which the user may type (or otherwise directly input) the appropriate value, or may be a drop down list from which the user may select the desired value. Values that may be included in a drop down list may include, for example, 0.5 pounds, 1 pound, 1.5 pounds, or 2 pounds. Using the user's desired weekly weight loss goal the user's weight goal after 12 weeks may be calculated by multiplying the weekly weight loss goal by 12 and subtracting that number from the user's starting weight. Thus, for example, the user whose data is shown in FIG. 4A has expressed a desire to lose 1 pound/week. After 12 weeks, the user will (hopefully) have lost 12 pounds, so his weight at that point will be 202-12=190 pounds.

There may be a correlation between the number of calories the user must "save" each day (relative to the estimated daily calorie needs) and the weekly weight loss goal. There are 3500 calories in 1 pound. So, by multiplying 3500 by the weekly weight loss goal and dividing by 7 (the number of days in a week), the number of calories that the user must "save" each day to achieve the weekly weight loss goal may be estimated. Table 2 shows this correlation:

TABLE 2

| Weekly Weight Loss Goal | Calorie Loss |
| --- | --- |
| 0.5 pounds/week | 250 |
| 1.0 pound/week | 500 |
| 1.5 pounds/week | 750 |
| 2.0 pounds/week | 1000 |

Figure 4B:
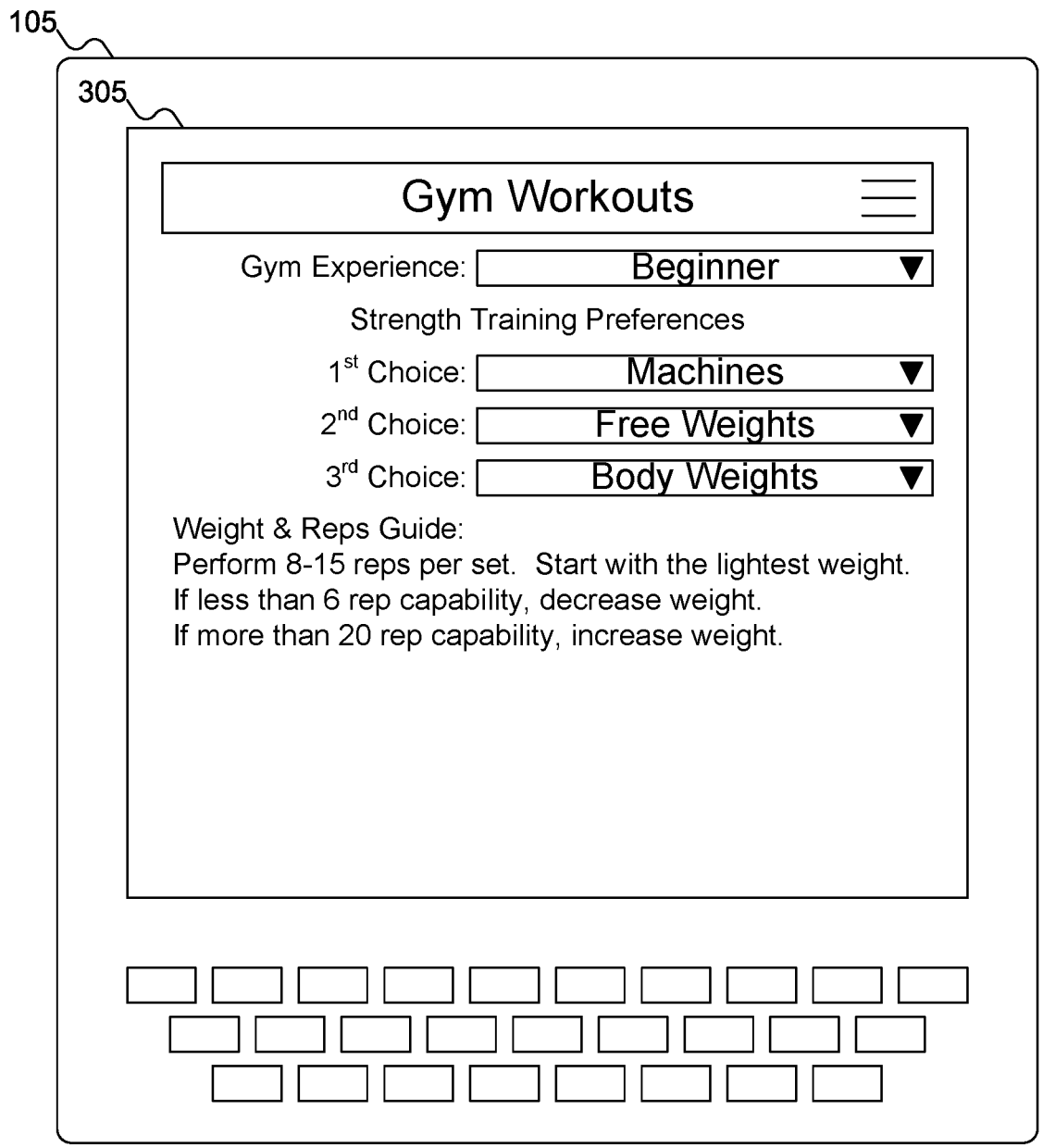

In FIG. 4B, screen 305 may present the user with options regarding choices for workouts in a gym. The user may specify his or her level of gym experience. The user may, for example, specify his or her level of gym experience as "beginner", "intermediate", or "advanced". The user may also specify their preference among different types of gym equipment. The equipment choices may be, for example, "machines", "free weights", and "body weights". As the choices for values in these fields may be limited, these fields may be drop down lists from which the user may select the desired values, rather than fields into which the user may type (or otherwise directly input) the appropriate values. Thus, for example, in FIG. 4B, the user has specified he is a beginner at using gym equipment, and prefers machines over free weights over body weights.

Application 130 of FIG. 1 may use this information in selecting various exercises that the user may perform to achieve an improved level of fitness. For example, the exercises presented for a beginning user who prefers to use machines may differ from an advanced user who prefers machines, which may differ from an advanced user who prefers free weights. Application 130 of FIG. 1 may store suggested exercises for each muscle or muscle group in the body for different levels of gym experience and for each type of equipment. The user may then be presented with a screen suggesting various exercises that may be used to target specific muscles or muscle groups. Application 130 of FIG. 1 may offer the user alternative exercises, if the user does not like a particular exercise, and may include photos or video showing how to perform the exercise. Application 130 of FIG. 1 may also permit the user to specify when the exercise has been completed, allowing application 130 of FIG. 1 to track the user's exercise.

As seen in FIG. 4B, screen 305 may also include comments for the user, such as how many repetitions to perform for each set, and when to increase or decrease the weight used for a particular set. In some embodiments of the invention, a user may perform three sets of repetitions of a particular exercise, each set at a different weight level. Screen 305 may also give the user some advice regarding warming up and/or warming down: for example, that the user should spend 10 minutes walking, running, using a exercise bicycle, climbing stairs, or using an elliptical machine, before beginning to exercise.

Figure 4C:
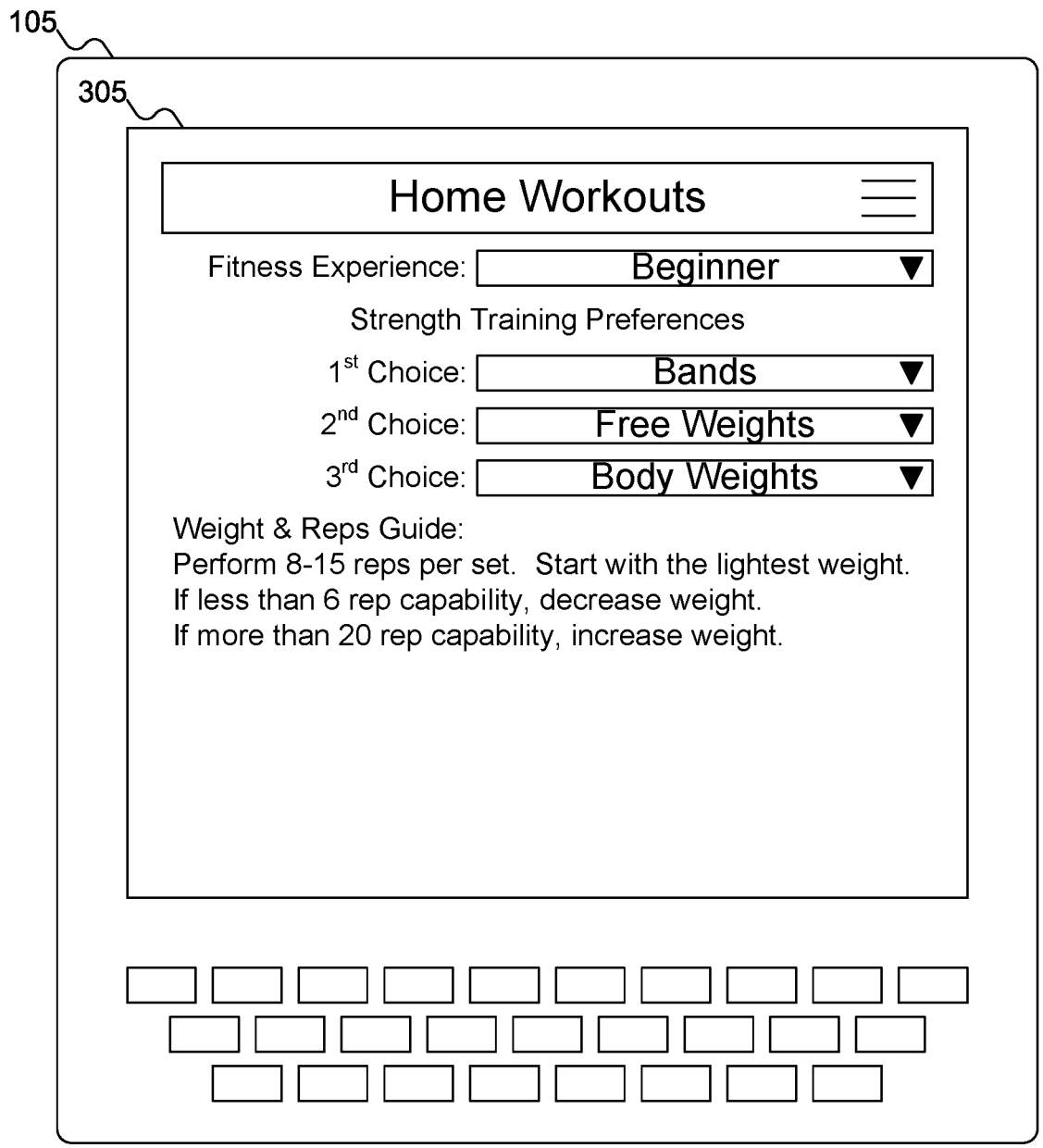

In FIG. 4C, screen 305 may present the user with options regarding choices for workouts at home. The user may specify his or her level of fitness experience. The user may, for example, specify his or her level of fitness experience as "beginner", "intermediate", or "advanced". The user may also specify their preference among different types of exercise equipment commonly used at home. The equipment choices may be, for example, "bands", "free weights", and "body weights". As the choices for values in these fields may be limited, these fields may be drop down lists from which the user may select the desired values, rather than fields into which the user may type (or otherwise directly input) the appropriate values. Thus, for example, in FIG. 4C, the user has specified he is a beginner at fitness, and prefers bands over free weights over body weights.

Application 130 of FIG. 1 may use this information in selecting various exercises that the user may perform to achieve an improved level of fitness. For example, the exercises presented for a beginning user who prefers to use bands may differ from an advanced user who prefers bands, which may differ from an advanced user who prefers free weights. Application 130 of FIG. 1 may store suggested exercises for each muscle or muscle group in the body for different levels of fitness and for each type of equipment. The user may then be presented with a screen suggesting various exercises that may be used to target specific muscles or muscle groups. Application 130 of FIG. 1 may offer the user alternative exercises, if the user does not like a particular exercise, and may include photos or video showing how to perform the exercise. Application 130 of FIG. 1 may also permit the user to specify when the exercise has been completed, allowing application 130 of FIG. 1 to track the user's exercise.

As seen in FIG. 4C, screen 305 may also include comments for the user, such as how many repetitions to perform for each set, and when to increase or decrease the weight used for a particular set. In some embodiments of the invention, a user may perform three sets of repetitions of a particular exercise, each set at a different weight level. Screen 305 may also give the user some advice regarding warming up and/or warming down: for example, that the user should spend 10 minutes walking, running, using a exercise bicycle, climbing stairs, or using an elliptical machine, before beginning to exercise.

Figure 4D:
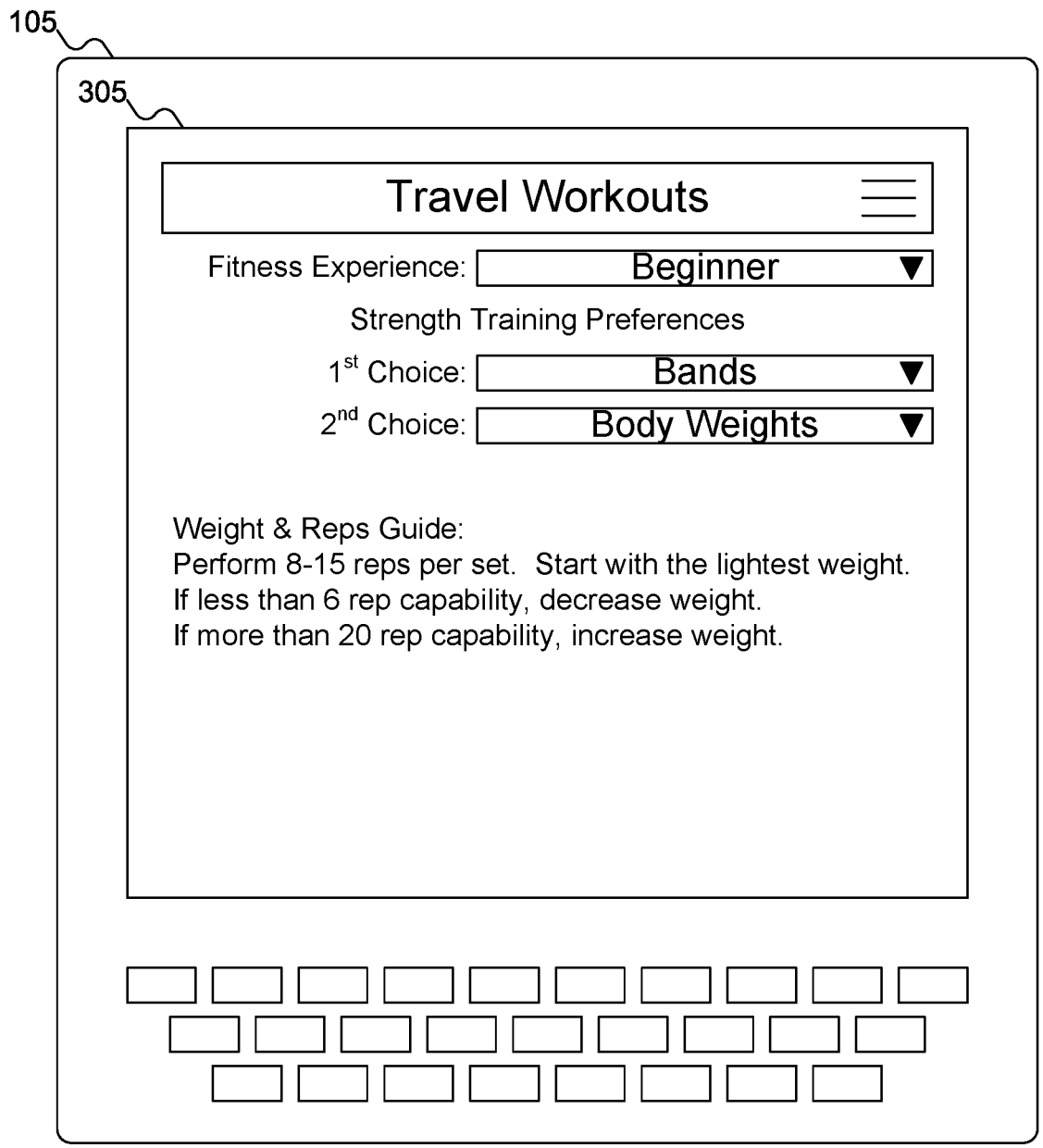

In FIG. 4D, screen 305 may present the user with options regarding choices for workouts while traveling. The user may specify his or her level of fitness experience. The user may, for example, specify his or her level of fitness experience as "beginner", "intermediate", or "advanced". (While generally the user's fitness level at home and while traveling may be expected to be the same, it is possible that the availability of exercise equipment at home and while traveling may vary, which in turn may affect how qualified the user feels regarding fitness when working out at home vs. working out while traveling. Thus, the user may have the option to input different levels of fitness at home vs. traveling.) The user may also specify their preference among different types of exercise equipment commonly used while traveling. The equipment choices may be, for example, "bands" and "body weights" (as free weights might not be readily available while traveling). As the choices for values in these fields may be limited, these fields may be drop down lists from which the user may select the desired values, rather than fields into which the user may type (or otherwise directly input) the appropriate values. Thus, for example, in FIG. 4D, the user has specified he is a beginner at fitness, and prefers bands over body weights.

Application 130 of FIG. 1 may use this information in selecting various exercises that the user may perform to achieve an improved level of fitness. For example, the exercises presented for a beginning user who prefers to use bands may differ from an advanced user who prefers bands, which may differ from an advanced user who prefers body weights. Application 130 of FIG. 1 may store suggested exercises for each muscle or muscle group in the body for different levels of fitness and for each type of equipment. The user may then be presented with a screen suggesting various exercises that may be used to target specific muscles or muscle groups. Application 130 of FIG. 1 may offer the user alternative exercises, if the user does not like a particular exercise, and may include photos or video showing how to perform the exercise. Application 130 of FIG. 1 may also permit the user to specify when the exercise has been completed, allowing application 130 of FIG. 1 to track the user's exercise.

As seen in FIG. 4D, screen 305 may also include comments for the user, such as how many repetitions to perform for each set, and when to increase or decrease the weight used for a particular set. In some embodiments of the invention, a user may perform three sets of repetitions of a particular exercise, each set at a different weight level. Screen 305 may also give the user some advice regarding warming up and/or warming down: for example, that the user should spend 10 minutes walking, running, using a exercise bicycle, climbing stairs, or using an elliptical machine, before beginning to exercise.

In FIGS. 4B-4D, screen 305 may also present the user with the option of performing interval training. Adding interval training to the exercise regimen may enhance the results of a workout. Interval training may include, for example, exercises that focus on the user's core, the user's abdomen, stretching, and the user's heart health. Application 130 of FIG. 1 may store various different combinations of interval training exercises that the user may perform, which may vary depending on the user's level of fitness and/or what exercises the user has performed (that day or in the past, since it may be beneficial to vary the exercises on different days).

Figure 4E:
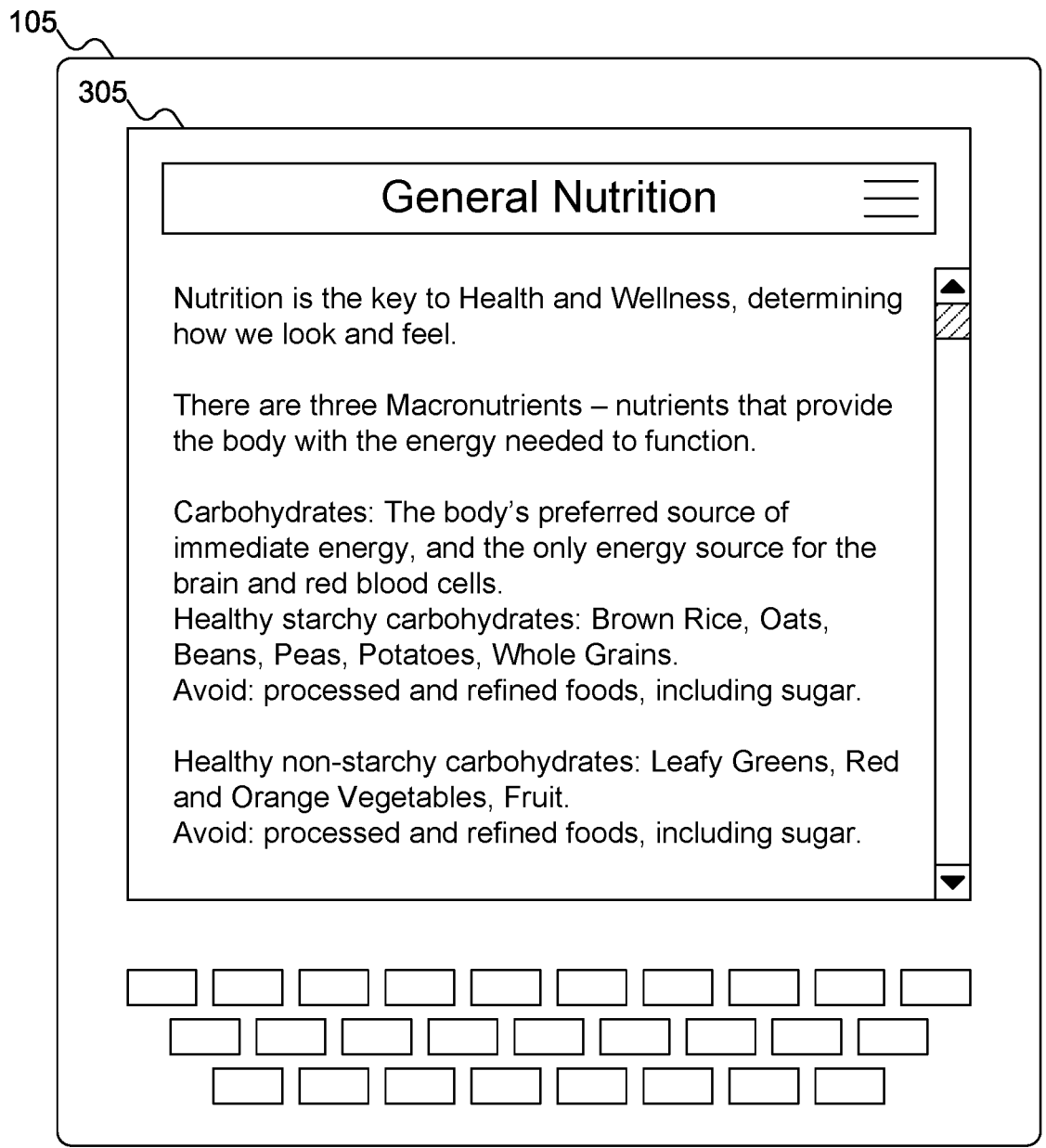

In FIG. 4E, screen 305 may present the user with general information regarding nutrition. This information may include discussions about various macronutrients such as carbohydrates, proteins, and fats, and may include suggestions regarding what foods are considered good choices vs. bad choices for different macronutrients. As shown by the slider bar, the information presented in FIG. 4E may represent only a portion of the information available to the user, and the user may review additional information by moving the slider bar (or otherwise scrolling through the content).

Figure 4F:
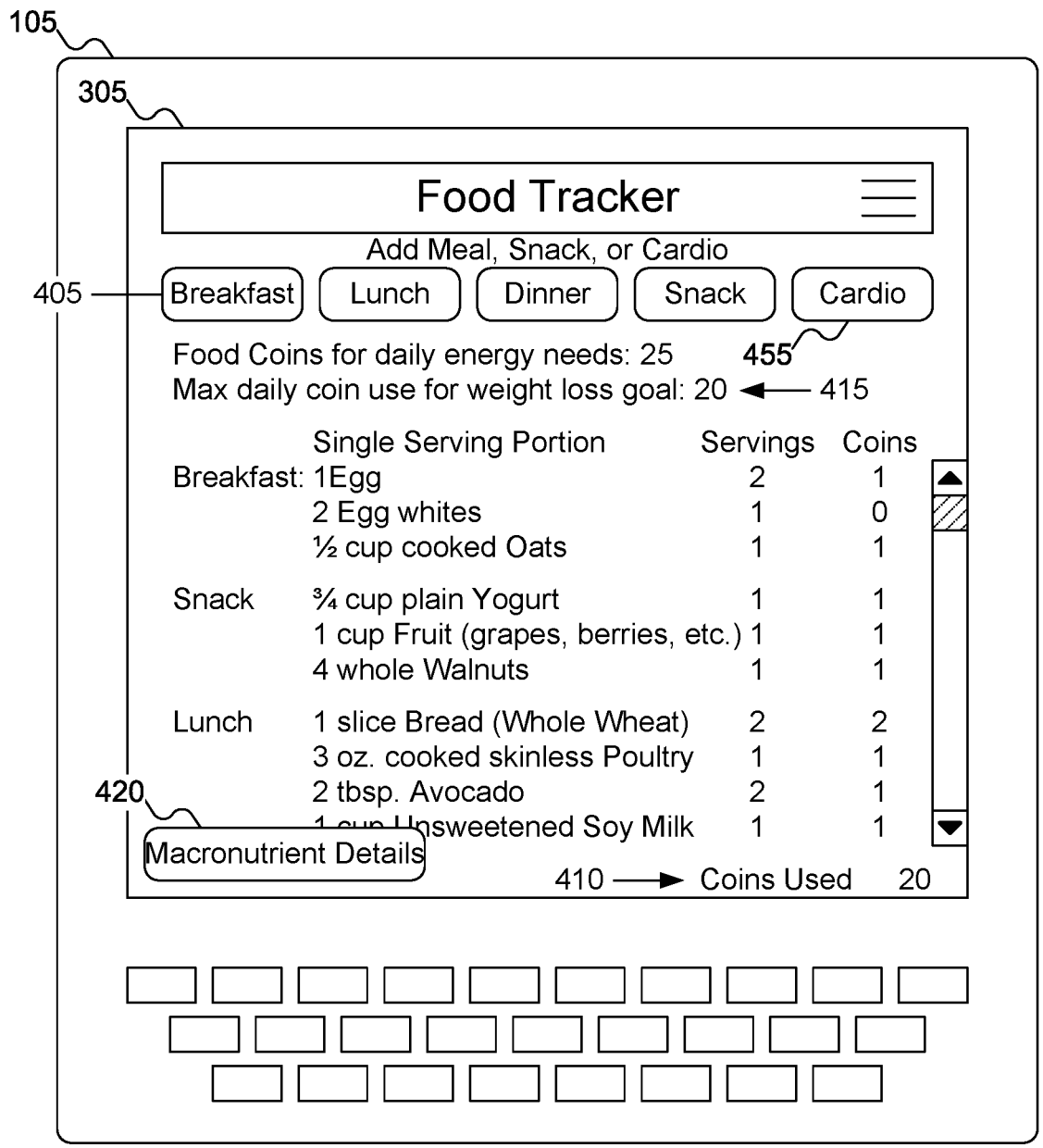

In FIG. 4F, screen 305 may present the user with the ability to track the foods the user has consumed. As shown in FIG. 4F, screen 305 may include buttons that let the user add foods (and servings of those foods) consumed at various times of the day. For example, breakfast button 405 may be used to add a food consumed at breakfast; other buttons may be used to add a food consumed at lunch, dinner, or for a snack.

When the user presses a button (such as breakfast button 405), application 130 of FIG. 1 may present the user with a list of foods, which may be stored in a table. The user may then scroll through the list to find the food consumed, and may enter the number of servings of the food the user consumed. The number of servings may be a field into which the user may type (or otherwise directly input) the appropriate value, or may be a drop down list from which the user may select the desired value. For example, the options for number of servings may be ⅛, ¼, ⅓, ⅜, ½, ⅝, ¾, ⅞, 1, 1⅛, 1¼, 1⅓, 1⅜, 1½, 1⅝, 1⅔, 1¾, 1⅞, and 2. The list of foods may also be filtered: for example, if the user pressed breakfast button 405 to enter a breakfast food, the list of foods may be filtered to show only the foods normally consumed at breakfast. Alternatively, the user may type the name of the food (using the keyboard) to search the list for the specific food consumed, or may speak the name of the food into a microphone, which may then be recognized using speech recognition software (running either on smartphone 105 or remotely accessed via a network connection). Application 130 of FIG. 1 may then add the food, the number of servings, and the number of coins used to a table storing foods consumed by the user.

Another way the user may add a food consumed is to manually enter information about a serving of the food into application 130 of FIG. 1. For example, the user may enter the name of the food and the number of grams of carbohydrates, proteins, and fats in a serving of the food, as well as the number of servings consumed. The user may also enter the number of milligrams of sodium in the serving of food, which may be used to track the user's sodium intake as described below. Application 130 of FIG. 1 may then add this food to the table of foods application 130 of FIG. 1 recognizes, and may calculate the number of coins associated with a serving of the food.

The number of coins for a serving of food may be computed from the number of grams of carbohydrates, proteins, and fats in the serving of the food, using the equation shown in Equation (4), where C is the number of grams of carbohydrates in the serving of the food, P is the number of grams of proteins in the serving of the food, and F is the number of grams of fats in the serving of the food:

$$\text{Number of Coins} = \frac{(4 \times C) + (4 \times P) + (9 \times F)}{100} \quad \text{Equation (4)}$$

The table stored in application 130 of FIG. 1 may store the food and associate with the food the number of coins used by consuming a serving of the food. The table may also store the number of grams of carbohydrates, proteins, and fats in the food, in which case the number of coins may be calculated when needed rather than stored in the table (although the number of coins may be stored alongside the number of grams of carbohydrates, proteins, and fats in a serving of the food).

Screen 305 also shows the list of foods the user has consumed today. These foods may be organized by type of meal: for example, if the user presses breakfast button 405 to enter the food, the food may be entered as a breakfast food. Application 130 of FIG. 1 may also track the number of coins the user has used today, as shown by total 410.

Screen 305 also shows the user a number of coins that corresponds to the user's estimated daily calorie needs, along with recommended number 415 of coins. Recommended number 415 of coins may represent the number of coins the user should consume to achieve the user's weekly weight loss goal, as discussed with reference to FIG. 4A above. Each coin corresponds to roughly 100 calories: so by taking the number of calories the user should save each day (shown in Table 2 above) and dividing by 100 (potentially with appropriate rounding), the number of coins the user should save each day to achieve the weekly weight loss goal may be estimated. But since coins also represent macronutrients: carbohydrates, proteins, and fats, coins are more than a substitute for calories.

One thing that FIG. 4F does not show is sodium intake. Sodium is an important compound for bodily health: consuming too little or too much sodium may be bad for the body. Each food the user consumes may have include some sodium. The amount of sodium in a particular serving of food may be independent of other information, such as the macronutrients in the serving of food or the number of coins used to consume that serving of food. Application 130 of FIG. 1 may track the amount of sodium consumed by the user on a daily basis, and may compare the amount of sodium consumed by the user with a recommended daily amount. If the user has consumed more sodium than recommended (or has consumed more sodium at a particular point during the day that is out of proportion with the amount of food consumed or coins used), application 130 of FIG. 1 may advise the user that his or her sodium consumption is out of balance with his or her overall food consumption. In this manner, the user may adjust what foods he or she eats to bring his or her sodium consumption back into balance. Application 130 of FIG. 1 may even suggest various foods that are low or high in sodium (depending on the user's total sodium consumption) to bring sodium intake back into balance. Application 130 of FIG. 1 may use different recommended daily sodium consumption levels for different individuals. For example, the recommended daily sodium intake may be 2300 mg/day for low-risk individuals (that is, individuals with a low risk for cardiovascular disease) and 1500 mg/day for high-risk individuals.

Figure 4G:
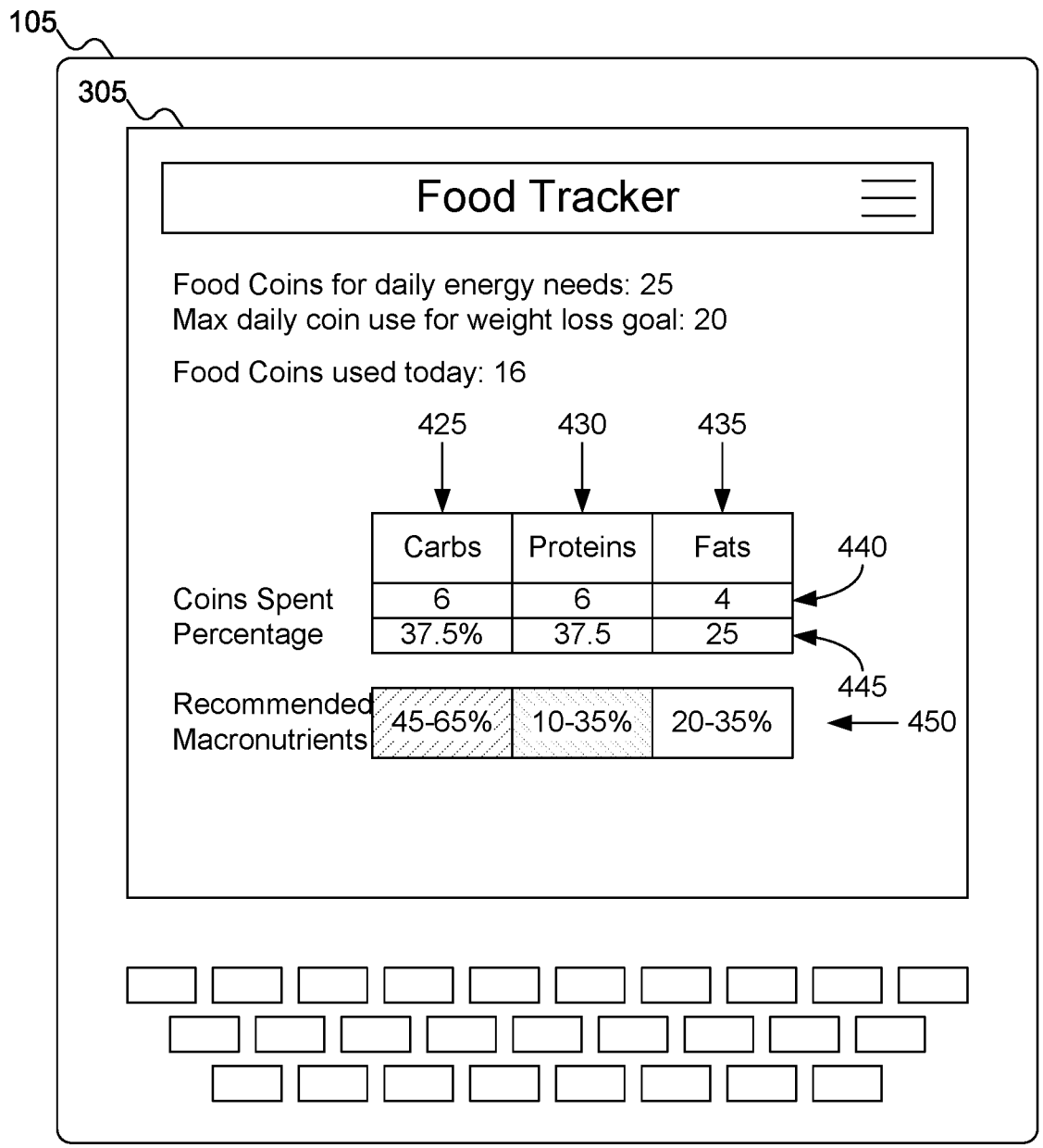

While tracking total number of coins 410 that the user has consumed on a daily basis provides an overall view of the user's health, some of the finer details may be missing. For example, if the user has consumed too many proteins and not enough carbohydrates, total number of coins 410 might not reflect this fact. By pressing recommended macronutrients button 420, the user may gain additional insight into his overall macronutrient consumption. FIG. 4G shows how this information may be presented to the user.

In FIG. 4G, screen 305 may show a table that details how many carbohydrates 425, proteins 430, and fats 435 the user has consumed. This information may presented by showing number of coins 440 the user has consumed as carbohydrates, proteins, and fats, or this information may be presented as percentage 445 of the coins used. Using this information, the user may see whether the foods he or she has consumed are biased in favor of (or against) particular macronutrients.

Although Equation (4) describes coins as being calculated from the number of grams of carbohydrates, proteins, and fats, the number of coins consumed by the user with respect to each macronutrient are easily derived from Equation (4). If the total of all grams of, say, carbohydrates by the user today are determined (which may be determined from the table storing what foods the user has consumed today), that number may be used for C in Equation (4). If P and F are set to zero, then the total number of coins calculated using Equation (4) may the number of coins of carbohydrates the user has consumed. In a similar manner, the number of coins of proteins and fats consumed by the user may be calculated.

Screen 305 may also include recommended macronutrients 450. Recommended macronutrients 450 may inform the user what percentage of foods consumed by the user should be carbohydrates, proteins, and fats. For example, since the user has consumed 16 coins so far today, with 6 of those coins used for fats, 37.5% of the user's coins have been "spent" on carbohydrates. Since the recommended daily percentage of coins may be, for example, 45-65%, the user has not consumed the recommended percentage of carbohydrates. Similarly, the user has consumed 37.5% of his or her coins as proteins, in excess of the recommended 10-35%. Thus, the entries for these macronutrients in recommended macronutrients 450 may be highlighted (shown in FIG. 4G with cross-hatching). Since the user's consumption of both carbohydrates and proteins are outside the range of recommended macronutrients 450 but in different ways, the emphasis placed on these macronutrients may be the same or different.

Returning to FIG. 4F, screen 305 may also include cardio button 455. Cardio button 455 may be used by the user to inform application 130 of FIG. 1 that the user has undertaken some cardio exercise. By pressing cardio button 420, the user may be taken to a new screen, shown in FIG. 4H.

Figure 4H:
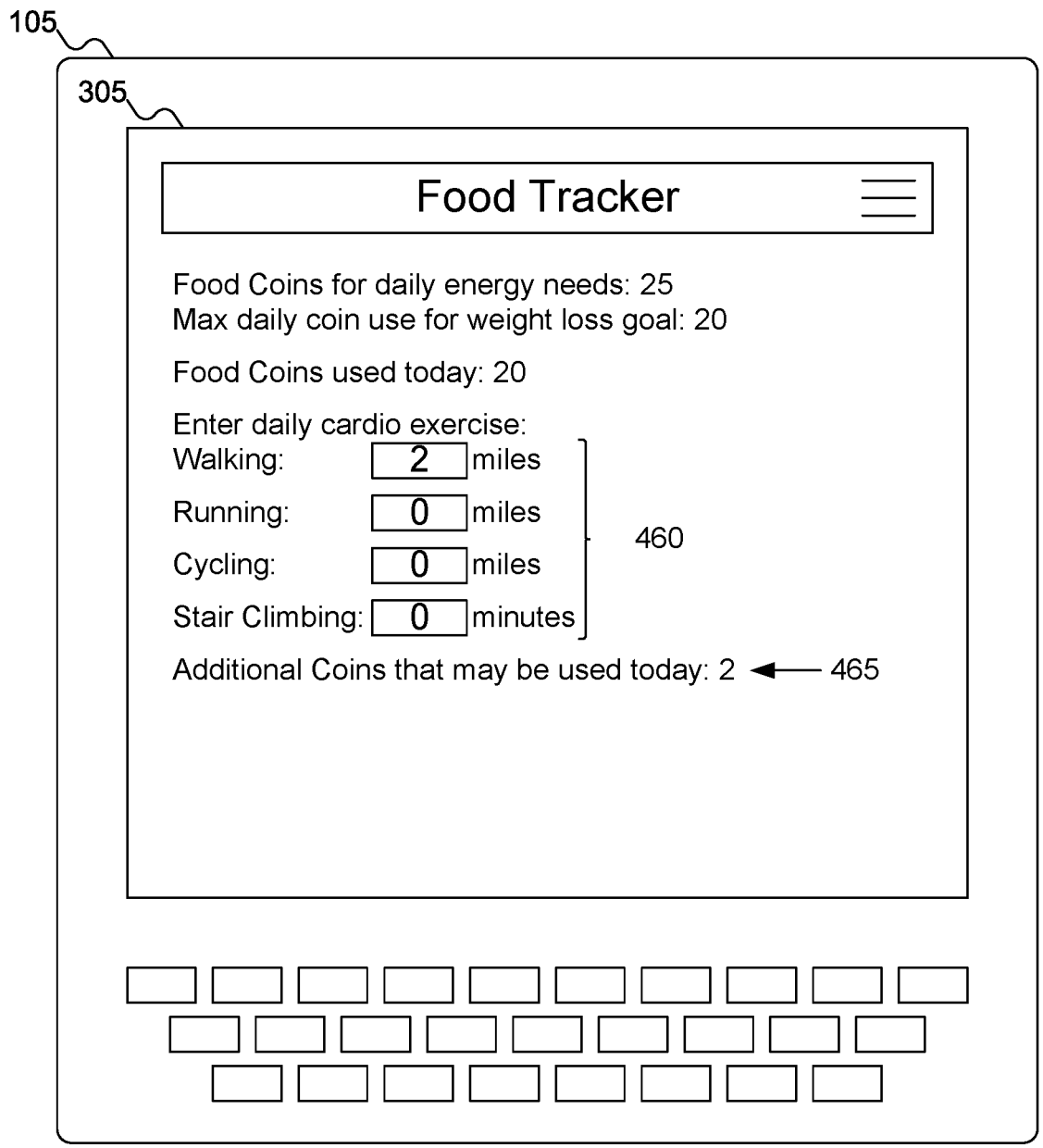

In FIG. 4H, screen 305 shows how the user may enter information about cardio exercise. Cardio exercise may be used to increase the number of coins the user may spend in a day.

As shown in FIG. 4H, the user may enter information about exercise 460. The user may enter, for example, a number of miles walked or run (which may be on a treadmill or outside: for example, in a park or in the streets), a number of miles cycled (which may be on an exercycle or outside), or a number of minutes of stair climbing performed (which may be on a stair climbing machine or by climbing flights of stairs). Using equations, application 130 of FIG. 1 may convert such exercises into additional coins the user may spend. For example, the user might earn one additional coin for every mile walked or run, for every three miles cycled, or for every 12½ minutes spent climbing stairs. As shown by additional coins 465, the user has earned two additional coins to spend by walking two miles.

While FIG. 4H describes coins being earned for cardio exercise, embodiments of the invention may permit the user to earn additional coins for any exercise. But since exercise may be part of a fitness regimen and application 130 of FIG. 1 may instruct the user to perform various exercises already, to count such exercises as both general fitness and for additional coins might overemphasize the value of exercise. Thus, exercises may be divided into two categories: those that are part of the general fitness regimen, and those that may earn additional coins.

FIG. 5 shows a table that may be used in application 130 of FIG. 1 to track foods consumed by the user, according to embodiments of the invention. In FIG. 5, table 505 is shown. Table 505 may include entries, such as entry 510. Entry 510 may represent a single food consumed by the user. Table 505 may track information such as food name 515, number of servings consumed 520, and number of coins spent 525. Thus, for example, in entry 510 the user consumed 2 servings of one egg each, spending a total of 1 coin. Other entries in table 505 may track other foods consumed by the user.

Table 505 is also shown including date 530. Date 530 may be used to track the particular day on which the food was consumed. By tacking the date on which the food was consumed, application 130 of FIG. 1 may use table 505 to access historical food consumed, allowing the user to revisit what foods were consumed on previous days. For example, application 130 of FIG. 1 may present the user with a calendar: the user may select a day on the calendar, and application 130 of FIG. 1 may then retrieve the foods consumed that day.

Although table 505 only shows the date being stored, embodiments of the invention may also store the time at which the food was consumed (or at least, entered into application 130 of FIG. 1). This additional information may be used to remind the user at what time the various foods were consumed. Table 505 may also track for which meal the food was consumed (for example, breakfast, lunch, dinner, or snack), in addition to or instead of the time at which the food was consumed. On the other hand, if application 130 of FIG. 1 only tracks what foods the user has consumed "today" and does not keep historical information, then date 530 might be omitted in some embodiments of the invention.

Although not shown in FIG. 5, table 505 may also track the macronutrients consumed by the user with each food consumed. By storing this information in table 505, application 130 of FIG. 1 may more easily determine the macronutrient information shown in FIG. 4G above. In addition, as discussed above with reference to FIG. 4F, application 130 of FIG. 1 may track sodium intake. The sodium in each food may also be stored in table 505, to support application 130 of FIG. 1 in tracking the user's sodium intake.

FIG. 6 shows a table that may be used in application 130 of FIG. 1 to determine a number of coins associated with a serving of food, according to embodiments of the invention. In FIG. 6, table 605 is shown. Table 605 may include entries, such as entry 610. Entry 610 may specify food name 525 and number of coins 525 associated with a single serving of the food. Table 605 may also include number of grams of carbohydrates 615, number of grams of proteins 620, and number of grams of fats 625 in a serving of the food. Note that table 605 might not track the number of servings like table 505 of FIG. 505, since table 605 is effectively a database of foods (single servings) that the user might consume; table 505, which tracks what foods the user has actually consumed on any given day, may track how many servings of each particular food the user has consumed on any particular day (and/or at any particular time).

Table 605 may also track additional information not shown in FIG. 6. For example, table 605 may include a column to track the typical meal(s) at which a particular food is eaten. For example, cooked Oats (entry 630) might normally be consumed at breakfast, whereas a slice of Whole Wheat Bread (entry 635) might be consumed at any meal or as a snack. Table 605 may also store the amount of sodium in each food, so that application 130 of FIG. 1 may track the user's daily sodium intake.

In FIGS. 4F-4G and 5-6, numbers 615, 620, and 625 of grams of carbohydrates, proteins, and fats, and number 525 of coins associated with a serving of food have been shown as whole numbers. In practice, these numbers might not always be whole numbers, but instead may include fractional or decimal portions. To simplify the presentation of information to the user, such information (particularly number 525 of coins associated with various servings of foods and numbers 440 of FIG. 4G) may be rounded to the nearest whole number. But behind the scenes, application 130 of FIG. 1 may manage such information with greater precision than whole numbers. This may explain why, for example, one egg (a single serving) may involve the user spending one coin (as shown in entry 610 of table 605), and yet two servings of one egg as consumed by the user may also involve the user spending one coin (as shown in entry 510 of FIG. 5 of table 505): a serving of one egg might actually only require spending, say, 0.6 coins, which may round up to 1 coin, but two servings of one egg might actually only require spending, say, 1.2 coins, which may round down to 1 coin as well.

Figure 7:
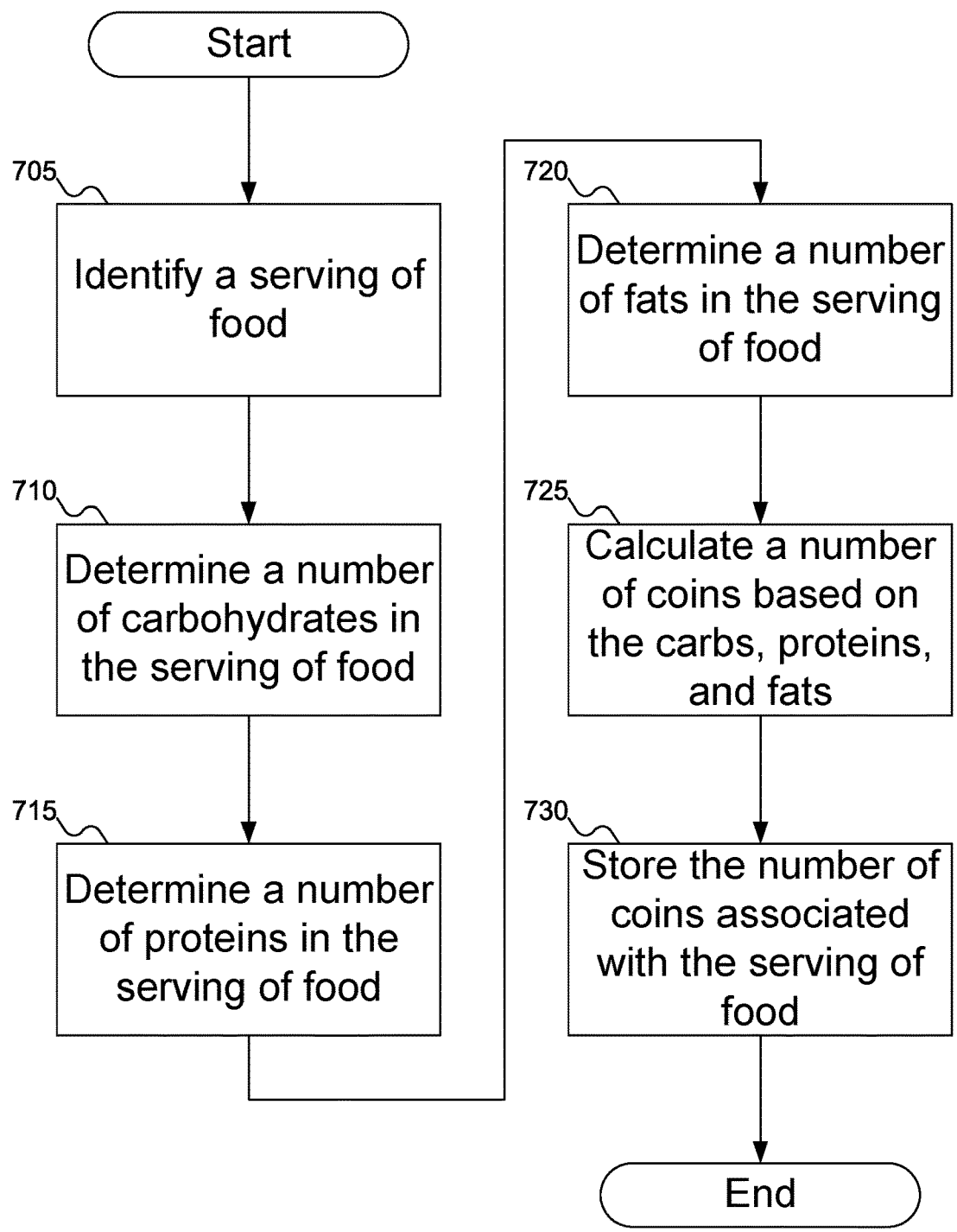
FIG. 7 shows a flowchart of an example procedure that the application of FIG. 1 may use to determine a number of coins associated with a serving of food, according to embodiments of the invention.

FIG. 7 shows a flowchart of an example procedure that application 130 of FIG. 1 may use to determine number of coins 525 of FIGS. 5-6 associated with a serving of food, according to embodiments of the invention. In FIG. 7, at block 705, application 130 of FIG. 1 may identify a serving of a food. At block 710, application 130 of FIG. 1 may determine the number of grams of carbohydrates in the serving of food. At block 715, application 130 of FIG. 1 may determine the number of grams of proteins in the serving of food. At block 720, application 130 of FIG. 1 may determine the number of grams of fats in the serving of food. Note that in blocks 710-720, application 130 of FIG. 1 may determine the number of grams of the macronutrients by accessing table 605 of FIG. 6 or some other table where such information is stored (if it is stored anywhere), or application 130 of FIG. 1 may receive such information via user interface 310 of FIG. 3 (for example, from the user in defining a new serving of food to be stored in application 130 of FIG. 1). At block 725, application 130 of FIG. 1 may calculate number of coins 525 of FIGS. 5-6 for the serving of food based on the number of grams of carbohydrates, proteins, and fats in the serving of food. For example, application 130 of FIG. 1 may use Equation (4) to determine number of coins 525 of FIGS. 5-6 for the serving of food. Finally, at block 730, application 130 of FIG. 1 may store number of coins 525 of FIGS. 5-6 in table 605 of FIG. 6, so that when the user indicates that he or she has consumed a serving of the food, number of coins 525 of FIG. 6 may be extracted from entries 605, 630, and/or 635 of FIG. 6 from table 605 of FIG. 6 and used in table 505 of FIG. 5 to track number of coins 410 of FIG. 4F spent by the user on a particular day. Alternatively, at block 730, application 130 of FIG. 1 may store number of coins 525 of FIGS. 5-6 in table 505 of FIG. 5 to reflect that the user has consumed a serving of food and spent number of coins 525 of FIGS. 5-6.

Figure 8A:
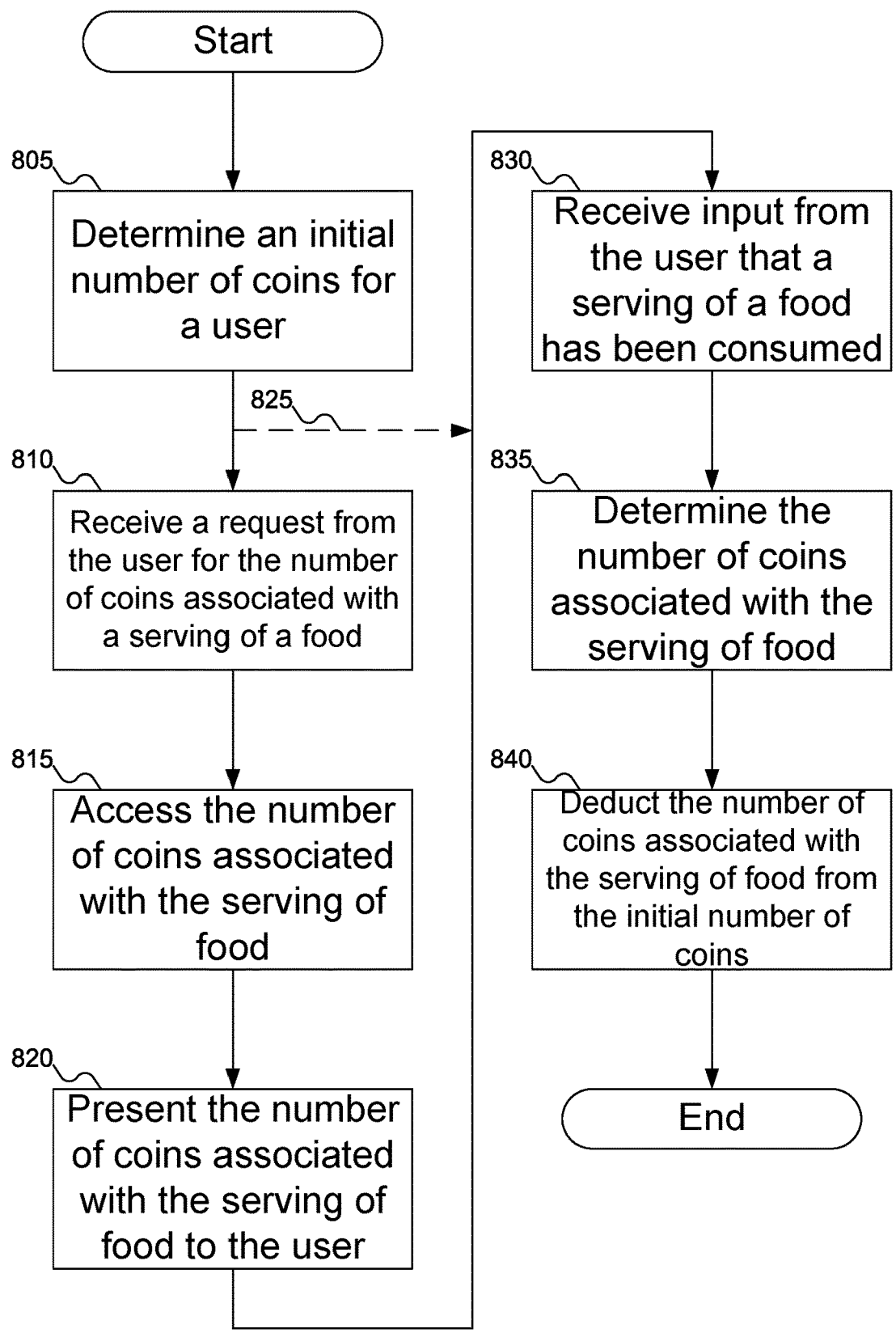
FIGS. 8A-8B show flowcharts of example procedures that the application of FIG. 1 may use to track foods consumed by the user, according to embodiments of the invention.
Figure 8B:
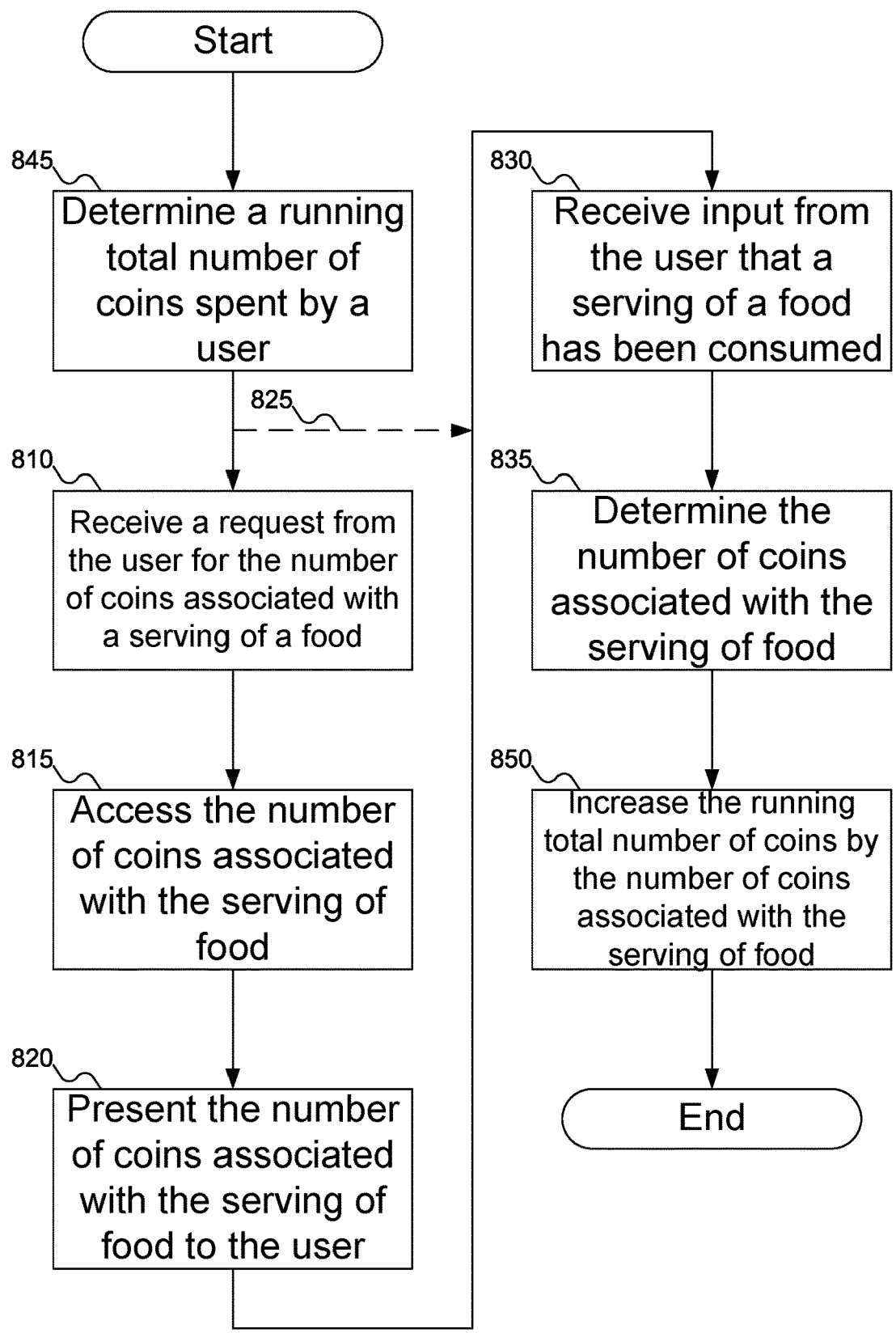

FIGS. 8A-8B show flowcharts of example procedures that the application of FIG. 1 may use to track foods consumed by the user, according to embodiments of the invention. In FIG. 8A, at block 805, application 130 of FIG. 1 may determine recommended number 415 of FIG. 4F of coins that the user may spend in a given day. At block 810, application 130 of FIG. 1 may receive a request from the user for the number 525 of FIG. 6 of coins associated with a serving of food. At block 815, application 130 of FIG. 1 may access number 525 of FIG. 6 of coins from table 605 of FIG. 6. Alternatively, at block 815, application 130 of FIG. 1 may access number 615 of FIG. 6 of grams of carbohydrates, number 620 of FIG. 6 of grams of proteins, and number 625 of FIG. 6 of grams of fats in the serving of food, and may then use Equation (4) to calculate number of coins 525 of FIG. 6. At block 820, application 130 of FIG. 1 may then present number 525 of FIG. 6 of coins to the user via a presentation system. Note that blocks 810, 815, and 820 may be omitted, as shown by dashed line 825.

At block 830, application 130 of FIG. 1 may receive information from the user—for example, via user interface 310—that the user has consumed a serving of the food. At block 835, application 130 of FIG. 1 may determine number 525 of FIG. 5 of coins associated with the serving of food. As discussed above, application 130 of FIG. 1 may determine number 525 of FIG. 5 of coins by accessing number 525 of FIG. 5 of coins associated with the serving of food from table 605 of FIG. 6, or by accessing number 615 of FIG. 6 of grams of carbohydrates in the serving of food, number 620 of FIG. 6 of grams of proteins in the serving of food, and number 625 of FIG. 6 of grams of fats in the serving of food, then calculating number 525 of FIG. 6 of coins using Equation (4). Finally, at block 840, application 130 of FIG. 1 may deduct number 525 of FIG. 6 of coins associated with the serving of food from recommended number 415 of FIG. 4F, resulting in the number of coins the user still has to spend.

In FIG. 8A, the focus is on starting with recommended number 415 of FIG. 4F of coins that the user may spend in a given day, and deducting coins spent by consuming food. In other embodiments of the invention, application 130 of FIG. 1 may instead keep a running total of coins spent by the user, rather than tracking the number of coins remaining to be spent by the user. FIG. 8B shows a flowchart of an example procedure that uses this approach instead.

In FIG. 8B, blocks that are identical or very similar to blocks in FIG. 8A use the same figure reference number; only blocks that are different have different figure reference numbers. In FIG. 8B, at block 845, application 130 of FIG. 1 may determine running total 410 of FIG. 4F of coins spent by the user in a given day. At block 810, application 130 of FIG. 1 may receive a request from the user for the number 525 of FIG. 6 of coins associated with a serving of food. At block 815, application 130 of FIG. 1 may access number 525 of FIG. 6 of coins from table 605 of FIG. 6. Alternatively, at block 815, application 130 of FIG. 1 may access number 615 of FIG. 6 of grams of carbohydrates, number 620 of FIG. 6 of grams of proteins, and number 625 of FIG. 6 of grams of fats in the serving of food, and may then use Equation (4) to calculate number of coins 525 of FIG. 6. At block 820, application 130 of FIG. 1 may then present number 525 of FIG. 6 of coins to the user via a presentation system. Note that blocks 810, 815, and 820 may be omitted, as shown by dashed line 825.

At block 830, application 130 of FIG. 1 may receive information from the user—for example, via user interface 310—that the user has consumed a serving of the food. At block 835, application 130 of FIG. 1 may determine number 525 of FIG. 5 of coins associated with the serving of food. As discussed above, application 130 of FIG. 1 may determine number 525 of FIG. 5 of coins by accessing number 525 of FIG. 5 of coins associated with the serving of food from table 605 of FIG. 6, or by accessing number 615 of FIG. 6 of grams of carbohydrates in the serving of food, number 620 of FIG. 6 of grams of proteins in the serving of food, and number 625 of FIG. 6 of grams of fats in the serving of food, then calculating number 525 of FIG. 6 of coins using Equation (4). Finally, at block 850, application 130 of FIG. 1 may increase running total 410 of FIG. 4F of coins spent by the user in a given day by number 525 of FIG. 6 of coins associated with the serving of food.

Figure 9A:
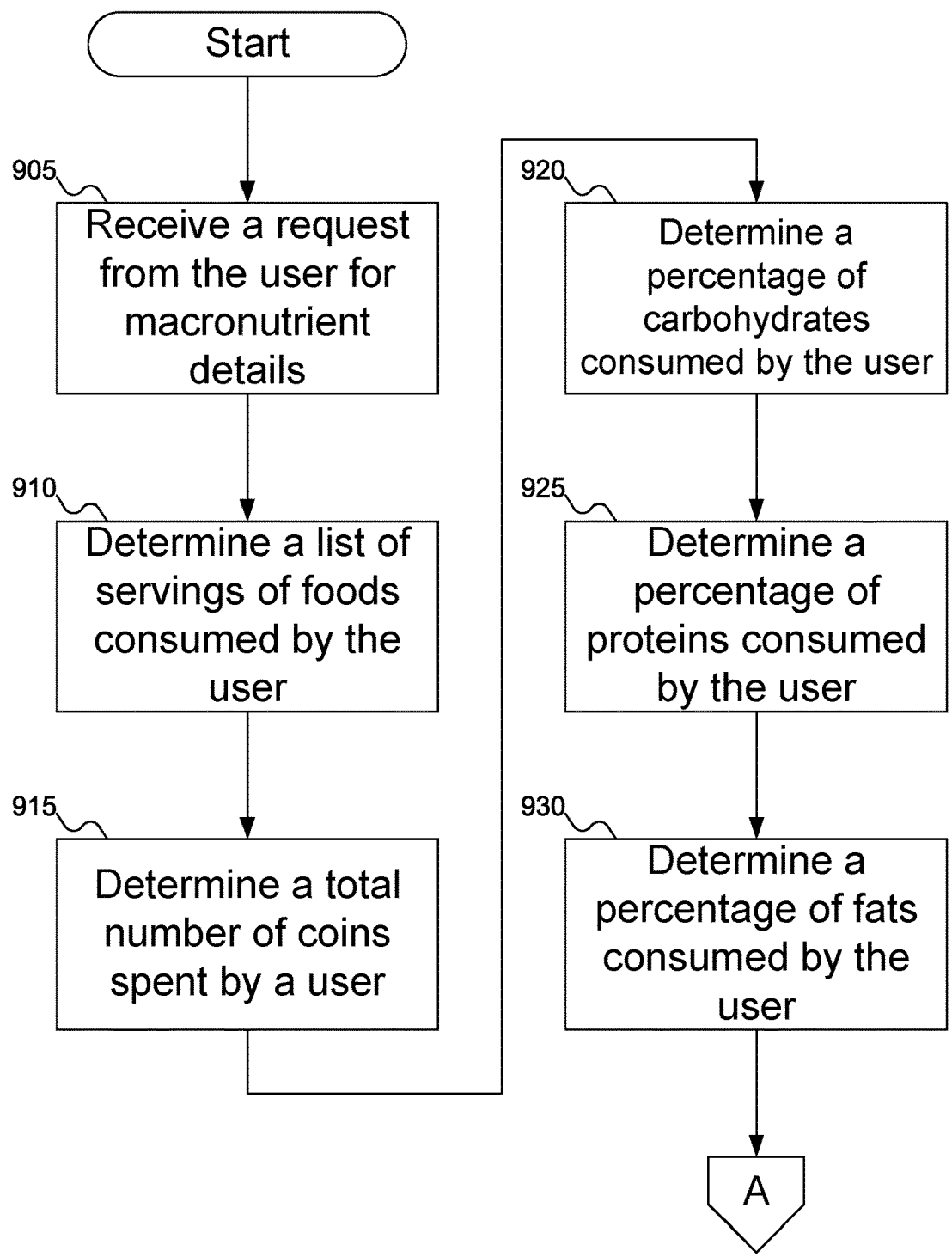
FIGS. 9A-9C show a flowchart of an example procedure that the application of FIG. 1 may use to inform the user about overall nutrition, according to embodiments of the invention.
Figure 9B:
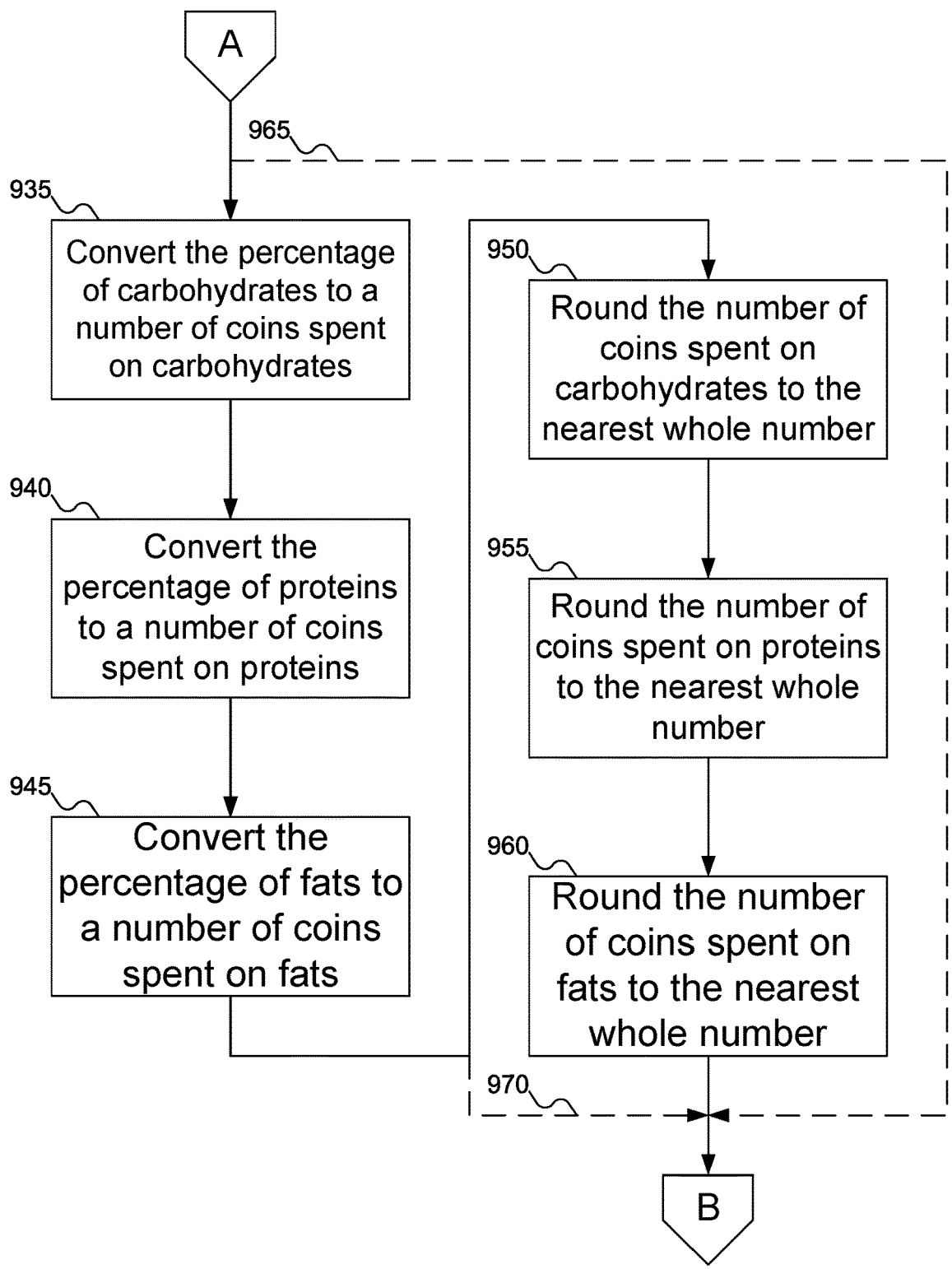
Figure 9C:
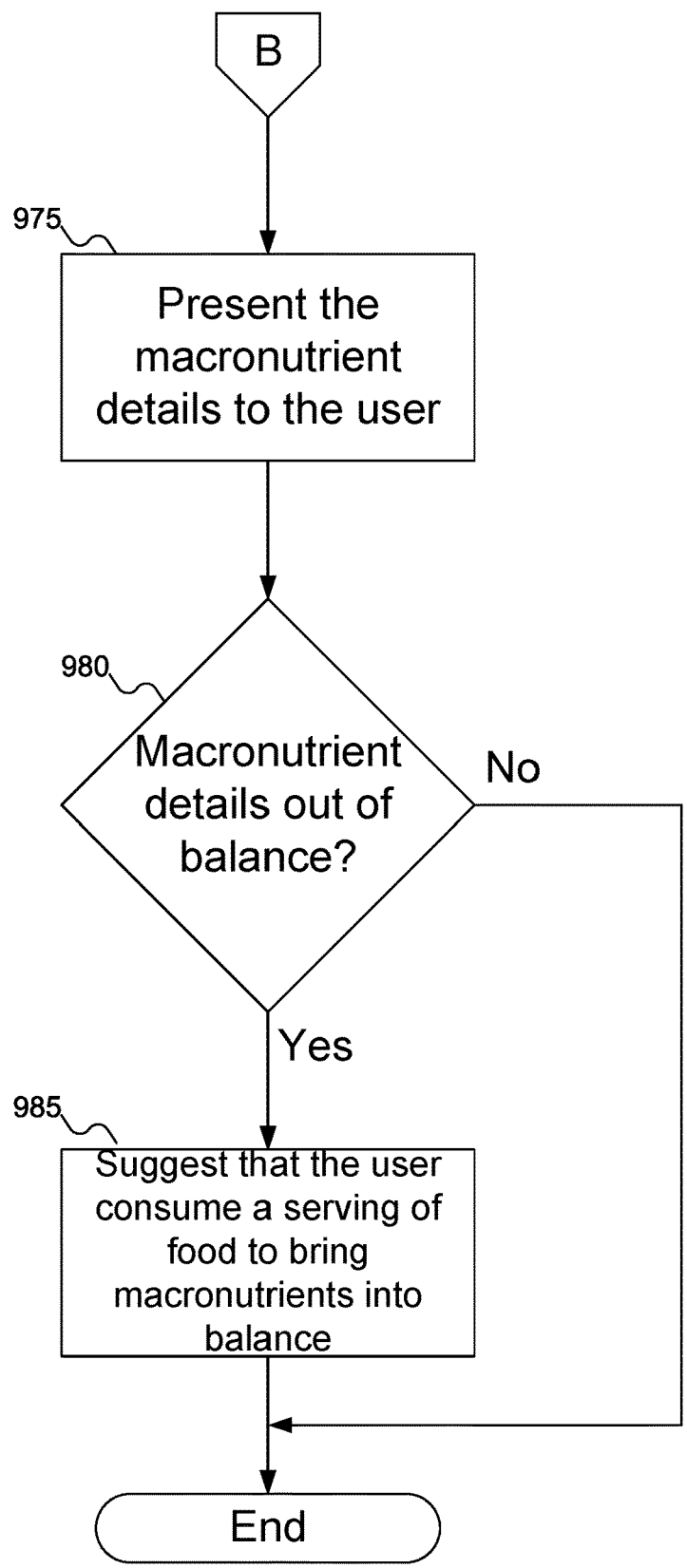

FIGS. 9A-9C show a flowchart of an example procedure that application 130 of FIG. 1 may use to inform the user about overall nutrition, according to embodiments of the invention. In FIG. 9A, at block 905, application 130 of FIG. 1 may receive from the user a request for macronutrient details about the foods consumed by the user. Application 130 of FIG. 1 may receive this information by, for example, detecting a press of macronutrients button 420 of FIG. 4F. At block 910, application 130 of FIG. 1 may determine a list of servings of foods consumed by the user: for example, by accessing table 505 of FIG. 5 (which may be filtered to identify just the servings of foods consumed that day). At block 915, application 130 of FIG. 1 may determine total number 410 of FIG. 4F of coins spent by the user that day: for example, by summing numbers 525 of FIG. 5 of coins in the servings of foods consumed that day by the user.

At block 920, application 130 of FIG. 1 may determine percentage 445 of FIG. 4G of coins spent on carbohydrates. At block 925, application 130 of FIG. 1 may determine percentage 445 of FIG. 4G of coins spent on proteins. And at block 930, application 130 of FIG. 1 may determine percentage 445 of FIG. 4G of coins spent on fats. These percentages may be calculated, for example, by accessing numbers 615, 620, and 625 of FIG. 6 of grams of carbohydrates, proteins, and fats in the servings of foods consumed by the user, totaling those numbers of grams of carbohydrates, proteins, and fats, computing the number of coins for each macronutrient, and determining the ratio of the number of coins for each macronutrient relative to total number 410 of FIG. 4F of coins spent by the user.

At block 935 (FIG. 9B), application 130 of FIG. 1 may convert percentage 445 of FIG. 4G of coins spent on carbohydrates into number 440 of FIG. 4G of coins spent on carbohydrates. At block 940, application 130 of FIG. 1 may convert percentage 445 of FIG. 4G of coins spent on proteins into number 440 of FIG. 4G of coins spent on proteins. At block 945, application 130 of FIG. 1 may convert percentage 445 of FIG. 4G of coins spent on fats into number 440 of FIG. 4G of coins spent on fats. Note that if application 130 of FIG. 1 computes number 440 of FIG. 4G of coins spent on each macronutrient first and then computes percentage 445 of FIG. 4G of coins spent on each macronutrient, the flowchart may be modified to say that application 130 of FIG. 1 computes number 440 of FIG. 4G of coins spent on each macronutrient first, then converts number 440 of FIG. 4G of coins spent on each macronutrient into percentage 445 of FIG. 4G of coins spent on each macro nutrient.

At block 950, application 130 of FIG. 1 may round number 440 of FIG. 4G of coins spent on carbohydrates to the nearest whole number. At block 955, application 130 of FIG. 1 may round number 440 of FIG. 4G of coins spent on proteins to the nearest whole number. At block 960, application 130 of FIG. 1 may round number 440 of FIG. 4G of coins spent on fats to the nearest whole number. Note that if application 130 of FIG. 1 only presents percentages 445 of FIG. 4G of each macronutrient to the user, then blocks 935-960 may be omitted, as shown by dashed line 965. Alternatively, the numbers 440 of FIG. 4G of coins spent on each macronutrient may be left unrounded (i.e., with fractional or decimal parts present), in which case blocks 950-960 may be omitted, as shown by dashed line 970.

At block 975 (FIG. 9C), application 130 of FIG. 1 may present the macronutrient details to the user, using, for example, the presentation system (such as screen 305 of FIG. 3). At block 980, application 130 of FIG. 1 may determine if any of the macronutrient details are out of balance: that is, the percentage of macronutrients consumed by the user so far in a given day may be outside the ranges of the recommended percentages for each macronutrients. If so, then at block 985, application 130 of FIG. 1 may identify which macronutrient(s) is/are out of balance, and may recommend to the user that the user consume a food that might bring the macronutrients back into balance. For example, application 130 of FIG. 1 may suggest a specific food could help bring the macronutrients back into balance, hopefully without having the user spend more than recommended number 415 of FIG. 4F of coins in a given day.

Figure 10:
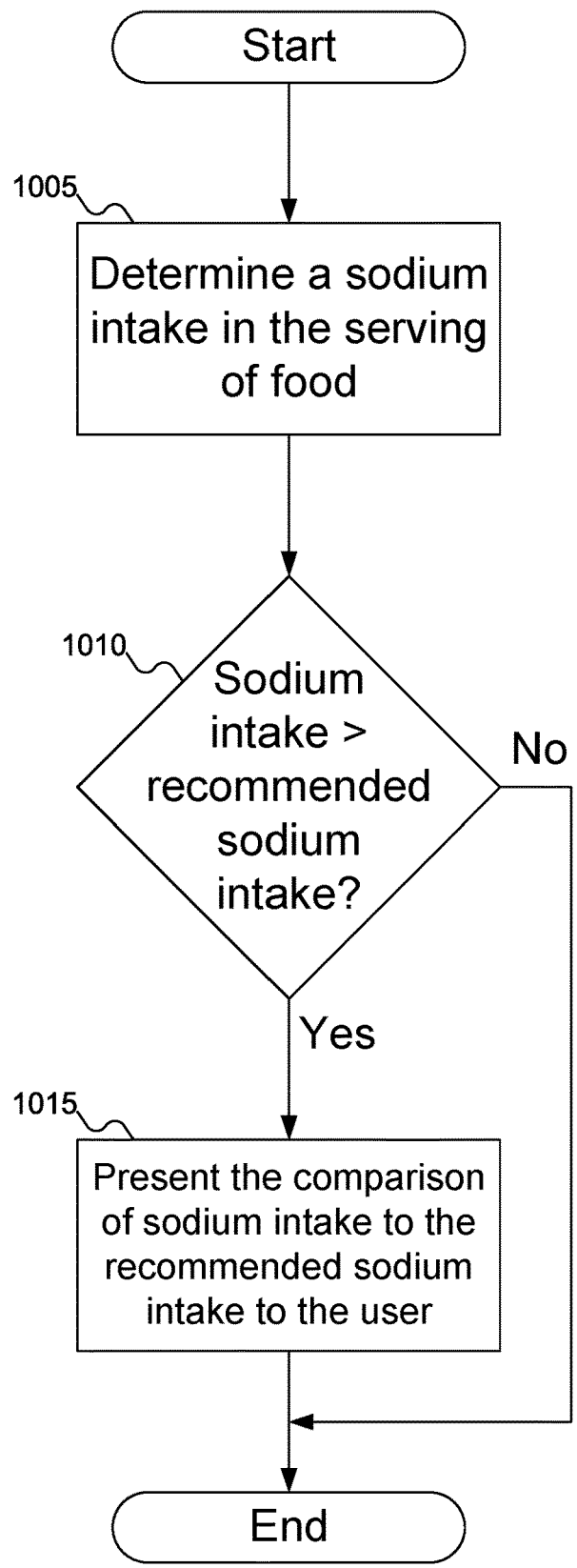
FIG. 10 shows a flowchart of an example procedure that the application of FIG. 1 may use to track the user's sodium intake, according to embodiments of the invention.

FIG. 10 shows a flowchart of an example procedure that application 130 of FIG. 1 may use to track the user's sodium intake, according to embodiments of the invention. In FIG. 10, at block 1005, application 130 of FIG. 1 may determine a sodium intake in a serving of food. At block 1010, application 130 of FIG. 1 may compare the sodium intake of the serving of food with a recommended sodium intake. If the sodium intake of the serving of food exceeds the recommended sodium intake, then at block 1015, application 130 of FIG. 1 may present this information to the user, so that the user may alter his or her food choices to prevent his or her sodium intake from exceeding the recommended sodium intake.

While FIG. 10 focuses on the sodium intake of a single food, embodiments of the invention may calculate the user's cumulative sodium intake for all foods consumed in a given day, and compare that total with the recommended sodium intake. Thus, while a single food might not, by itself, exceed the recommended sodium intake, the sodium in a single food might "push" the user above the recommended sodium intake for the day.

Figure 11:
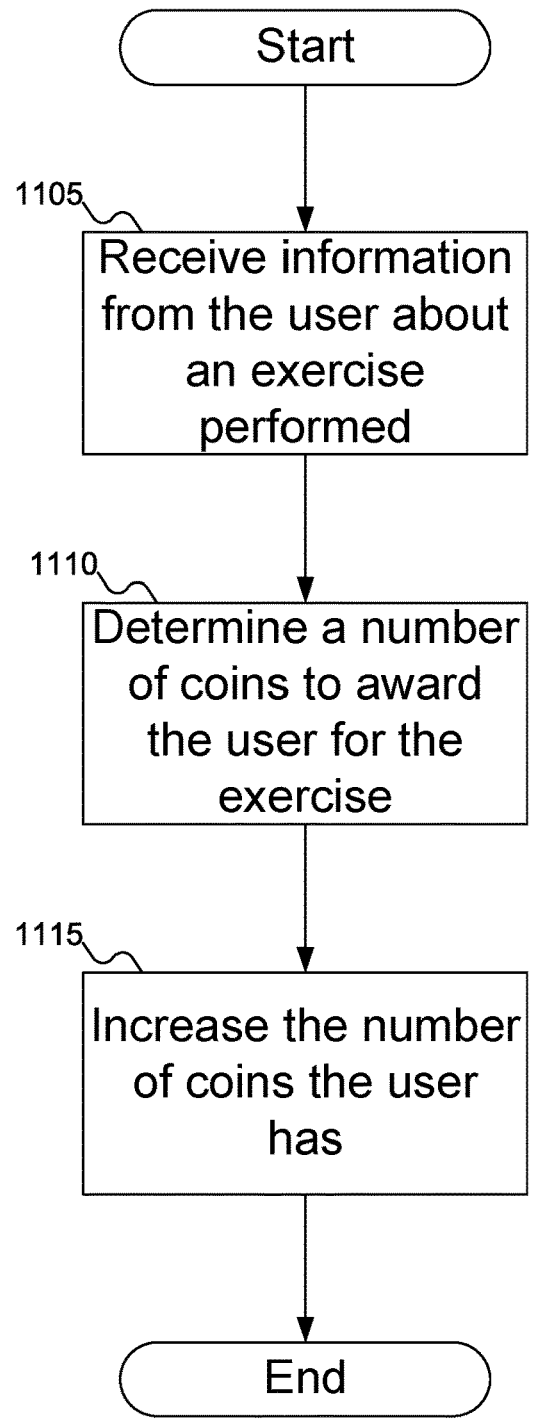
FIG. 11 shows a flowchart of an example procedure that the application of FIG. 1 may use to encourage exercise, according to embodiments of the invention.

FIG. 11 shows a flowchart of an example procedure that application 130 of FIG. 1 may use to encourage exercise, according to embodiments of the invention. In FIG. 11, at block 1105, application 130 of FIG. 1 may receive information from the user about an exercise performed. This exercise may be a cardio exercise, as discussed above with reference to FIG. 4H, and the information may include the distance covered during the exercise or the duration of the exercise (depending on the exercise in question). At block 1110, application 130 of FIG. 1 may determine a number of coins to award the user based on performing the exercise. As discussed above with reference to FIG. 4H, the number of coins to award may depend on the distance covered during the exercise, the duration of the exercise, and/or the exercise itself. Finally, at block 1115, application 130 of FIG. 1 may increase recommended number 415 of FIG. 4F of coins that the user may spend that day.

In FIGS. 7-11, some embodiments of the invention are shown. But a person skilled in the art will recognize that other embodiments of the invention are also possible, by changing the order of the blocks, by omitting blocks, or by including links not shown in the drawings. All such variations of the flowcharts are considered to be embodiments of the invention, whether expressly described or not.

Embodiments of the invention include some advantages. The application may track macronutrient consumption rather than just calories. Coins may be used to track macronutrients, providing the user with a way to measure whether the user is receiving balanced nutrition as well as managing diet for weight loss purposes. The application may also award additional coins for the user to spend in a given day if the user performs exercises.

The following discussion is intended to provide a brief, general description of a suitable machine or machines in which certain aspects of the invention may be implemented. The machine or machines may be controlled, at least in part, by input from conventional input devices, such as keyboards, mice, etc., as well as by directives received from another machine, interaction with a virtual reality (VR) environment, biometric feedback, or other input signal. As used herein, the term "machine" is intended to broadly encompass a single machine, a virtual machine, or a system of communicatively coupled machines, virtual machines, or devices operating together. Exemplary machines include computing devices such as personal computers, workstations, servers, portable computers, handheld devices, telephones, tablets, etc., as well as transportation devices, such as private or public transportation, e.g., automobiles, trains, cabs, etc.

The machine or machines may include embedded controllers, such as programmable or non-programmable logic devices or arrays, Application Specific Integrated Circuits (ASICs), embedded computers, smart cards, and the like. The machine or machines may utilize one or more connections to one or more remote machines, such as through a network interface, modem, or other communicative coupling. Machines may be interconnected by way of a physical and/or logical network, such as an intranet, the Internet, local area networks, wide area networks, etc. One skilled in the art will appreciate that network communication may utilize various wired and/or wireless short range or long range carriers and protocols, including radio frequency (RF), satellite, microwave, Institute of Electrical and Electronics Engineers (IEEE) 802.11, Bluetooth®, optical, infrared, cable, laser, etc.

Embodiments of the present invention may be described by reference to or in conjunction with associated data including functions, procedures, data structures, application programs, etc. which when accessed by a machine results in the machine performing tasks or defining abstract data types or low-level hardware contexts. Associated data may be stored in, for example, the volatile and/or non-volatile memory, e.g., RAM, ROM, etc., or in other storage devices and their associated storage media, including hard-drives, floppy-disks, optical storage, tapes, flash memory, memory sticks, digital video disks, biological storage, etc. Associated data may be delivered over transmission environments, including the physical and/or logical network, in the form of packets, serial data, parallel data, propagated signals, etc., and may be used in a compressed or encrypted format. Associated data may be used in a distributed environment, and stored locally and/or remotely for machine access.

Embodiments of the invention may include a tangible, non-transitory machine-readable medium comprising instructions executable by one or more processors, the instructions comprising instructions to perform the elements of the inventions as described herein.

Having described and illustrated the principles of the invention with reference to illustrated embodiments, it will be recognized that the illustrated embodiments may be modified in arrangement and detail without departing from such principles, and may be combined in any desired manner. And, although the foregoing discussion has focused on particular embodiments, other configurations are contemplated. In particular, even though expressions such as "according to an embodiment of the invention" or the like are used herein, these phrases are meant to generally reference embodiment possibilities, and are not intended to limit the invention to particular embodiment configurations. As used herein, these terms may reference the same or different embodiments that are combinable into other embodiments.

The foregoing illustrative embodiments are not to be construed as limiting the invention thereof. Although a few embodiments have been described, those skilled in the art will readily appreciate that many modifications are possible to those embodiments without materially departing from the novel teachings and advantages of the present disclosure. Accordingly, all such modifications are intended to be included within the scope of this invention as defined in the claims.

Embodiments of the invention may extend to the following statements, without limitation:

Statement 1. An embodiment of the invention includes a system (105), comprising:
  a processor (110);
  storage (120) for a table (505) of foods (515) consumed by a user, the table (505) associating a serving (520) of a food (515) with a number (525) of coins; and
  a presentation system (305) operative to inform the user that the user has spent too many coins based at least in part on a total (410) of the number (525) of coins in the table (505) exceeding a recommended number (415) of coins for the user,
  wherein the number (525) of coins associated with the serving (520) of the food (515) depends at least in part on a first number (615) of grams of carbohydrates in the serving (520) of the food (515), a second number (620) of grams of proteins in the serving (520) of the food (515), and a third number (625) of grams of fats in the serving (520) of the food (515).

Statement 2. An embodiment of the invention includes the system (105) according to statement 1, wherein the system (105) includes one of a computer and a smart device.

Statement 3. An embodiment of the invention includes the system (105) according to statement 1, further comprising a second table (605) associating the serving (520) of the food (515) with the number (525) of coins.

Statement 4. An embodiment of the invention includes the system (105) according to statement 3, wherein the second table (605) further associates the serving (520) of the food (515) with the first number (615) of grams of carbohydrates, the second number (620) of grams of proteins, and the third number (625) of grams of fats.

Statement 5. An embodiment of the invention includes the system (105) according to statement 1, further comprising a user interface (310) to receive the first number (615) of grams of carbohydrates, the second number (620) of grams of proteins, and the third number (625) of grams of fats from the user.

Statement 6. An embodiment of the invention includes the system (105) according to statement 1, wherein:

the system (105) further comprises a user interface (310) to receive a request for information about the serving (520) of food (515) from the user; and the presentation system (305) is operative to present the number (525) of coins associated with the serving (520) of food (515) to the user.

Statement 7. An embodiment of the invention includes the system (105) according to statement 1, wherein the processor (110) is operative to calculate a first percentage (445) of the total (410) of the number (525) of coins spent on carbohydrates, a second percentage (445) of the total (410) of the number (525) of coins spent on proteins, and a third percentage (445) of the total (410) of the number (525) of coins spent on fats.

Statement 8. An embodiment of the invention includes the system (105) according to statement 7, wherein the presentation system (305) is operative to present the first percentage (445) of the total (410) of the number (525) of coins spent on carbohydrates, the second percentage (445) of the total (410) of the number (525) of coins spent on proteins, and the third percentage (445) of the total (410) of the number (525) of coins spent on fats to the user.

Statement 9. An embodiment of the invention includes the system (105) according to statement 8, wherein the presentation system (305) is further operative to suggest (450) that the user consume a second serving (520) of a second food (515) to bring the first percentage (445) of the total (410) number coins spent on carbohydrates, the second percentage (445) of the total (410) number coins spent on proteins, and the third percentage (445) of the total (410) number coins spent on fats into balance.

Statement 10. An embodiment of the invention includes the system (105) according to statement 7, wherein:

the calculator is further operative to calculate a fourth number (440) of coins spent on carbohydrates, a fifth number (440) of coins spent on proteins, and a sixth number (440) of coins spent on fats; and the presentation system (305) is operative to present the fourth number (440) of coins spent on carbohydrates, the fifth the number (440) of coins spent on proteins, and the sixth number (440) of coins spent on fats to the user.

Statement 11. An embodiment of the invention includes the system (105) according to statement 1, wherein:

the table (505) of foods (515) consumed by a user is operative to associates the serving (520) of the food (515) with the number (525) of coins and a sodium intake; and the presentation system (305) is operative to present a comparison of the sodium intake relative to a recommended sodium intake to the user.

Statement 12. An embodiment of the invention includes the system (105) according to statement 1, wherein:

the system (105) further comprises a user interface (310) to receive an exercise (460) performed by the user; and the processor (110) is operative to adjust an initial number (525) of coins based at least in part on the exercise (460) performed.

Statement 13. An embodiment of the invention includes the system (105) according to statement 12, wherein the exercise (460) performed is drawn from a set including walking, running, bicycling, and stair climbing.

Statement 14. An embodiment of the invention includes a method, comprising:

identifying (705), in an application (130) running on a system (105), a serving (520) of a food (515) consumed by a user;

determining (710), by the application (130) running on the system (105), a first number (615) of grams of carbohydrates in the serving (520) of the food (515);

determining (715), by the application (130) running on the system (105), a second number (620) of grams of proteins in the serving (520) of the food (515);

determining (720), by the application (130) running on the system (105), a third number (625) of grams of fats in the serving (520) of the food (515); and calculating (725), by the application (130) running on the system (105), a number (525) of coins for the serving (520) of the food (515) based at least in part on the first number (615) of grams of carbohydrates, the second number (620) of grams of proteins, and the third number (625) of grams of fats.

Statement 15. An embodiment of the invention includes the method according to statement 14, further comprising storing (730) the number (525) of coins associated with the serving (520) of the food (515) in a table (505).

Statement 16. An embodiment of the invention includes the method according to statement 14, wherein:

determining (710), by the application (130) running on the system (105), the first number (615) of grams of carbohydrates in the serving (520) of the food (515) includes accessing (710), by the application (130) running on the system (105), the first number (615) of grams of carbohydrates in the serving (520) of the food (515) from a table (605);

determining (715), by the application (130) running on the system (105), the second number (620) of grams of proteins in the serving (520) of the food (515) includes accessing (715), by the application (130) running on the system (105), the second number (620) of grams of proteins in the serving (520) of the food (515) from the table (605); and determining (720), by the application (130) running on the system (105), the third number (625) of grams of fats in the serving (520) of the food (515) includes accessing (720), by the application (130) running on the system (105), the third number (625) of grams of fats in the serving (520) of the food (515) from the table (605).

Statement 17. An embodiment of the invention includes the method according to statement 14, wherein:

determining (710), by the application (130) running on the system (105), the first number (615) of grams of carbohydrates in the serving (520) of the food (515) includes receiving (710), at the application (130) running on the system (105), the first number (615) of grams of carbohydrates in the serving (520) of the food (515) from the user;

determining (715), by the application (130) running on the system (105), the second number (620) of grams of proteins in the serving (520) of the food (515) includes receiving (715), at the application (130) running on the system (105), the second number (620) of grams of proteins in the serving (520) of the food (515) from the user; and determining (720), by the application (130) running on the system (105), the third number (625) of grams of fats in the serving (520) of the food (515) includes receiving (720), at the application (130) running on the system (105), the third number (625) of grams of fats in the serving (520) of the food (515) from the user.

Statement 18. An embodiment of the invention includes the method according to statement 14, further comprising:

determining (805) an initial number (525) of coins for the user;

receiving (830) an input from the user that the serving (520) of the food (515) has been consumed; and deducting (840) the number (525) of coins from the initial number (525) of coins.

Statement 19. An embodiment of the invention includes the method according to statement 14, further comprising:

determining (845) a total (410) number of coins spent by the user;

receiving (830) an input from the user that the serving (520) of the food (515) has been consumed; and increasing (850) the total (410) number of coins spent by the user by the number (525) of coins.

Statement 20. An embodiment of the invention includes the method according to statement 14, further comprising:

receiving (810), by the application (130) running on the system (105), from the user a request for information about the serving (520) of the food (515); and presenting (820), by the application (130) running on the system (105), to the user the number (525) of coins associated with the serving (520) of the food (515).

Statement 21. An embodiment of the invention includes the method according to statement 14, further comprising:

determining (910), by the application (130) running on the system (105), a list of servings (520) of foods (515) consumed by the user;

determining (915), by the application (130) running on the system (105), a total (410) number of coins spent by the user;

determining (920), by the application (130) running on the system (105), a first percentage (445) of the total (410) number of coins spent on carbohydrates;

determining (925), by the application (130) running on the system (105), a second percentage (445) of the total (410) number of coins spent on proteins; and determining (930), by the application (130) running on the system (105), a third percentage (445) of the total (410) number of coins spent on fats.

Statement 22. An embodiment of the invention includes the method according to statement 21, further comprising:

receiving (905), at the application (130) running on the system (105), from the user a request for macronutrient details; and presenting (975), by the application (130) running on the system (105), to the user the first percentage (445) of the total (410) number of coins spent on carbohydrates, the second percentage (445) of the total (410) number of coins spent on proteins, and the third percentage (445) of the total (410) number of coins spent on fats.

Statement 23. An embodiment of the invention includes the method according to statement 21, further comprising:

determining (980), by the application (130) running on the system (105), that the first percentage (445) of the total (410) number of coins spent on carbohydrates, the second percentage (445) of the total (410) number of coins spent on proteins, and the third percentage (445) of the total (410) number of coins spent on fats are not balanced; and suggesting (985), by the application (130) running on the system (105), that the user consume a second serving (520) of a second food (515) to bring the first percentage (445) of the total (410) number of coins spent on carbohydrates, the second percentage (445) of the total (410) number of coins spent on proteins, and the third percentage (445) of the total (410) number of coins spent on fats into balance.

Statement 24. An embodiment of the invention includes the method according to statement 21, wherein presenting (820), by the application (130) running on the system (105), to the user the first percentage (445) of the total (410) number of coins spent on carbohydrates, the second percentage (445) of the total (410) number of coins spent on proteins, and the third percentage (445) of the total (410) number of coins spent on fats includes:

converting (935), by the application (130) running on the system (105), the first percentage (445) of the total (410) number of coins spent on carbohydrates into a fourth number (525) of coins spent on carbohydrates;

converting (940), by the application (130) running on the system (105), the second percentage (445) of the total (410) number of coins spent on proteins into a fifth number (525) of coins spent on proteins;

converting (945), by the application (130) running on the system (105), the third percentage (445) of the total (410) number of coins spent on fats into a sixth number (525) of coins spent on fats; and presenting (975), by the application (130) running on the system (105), to the user the fourth number (525) of coins spent on carbohydrates, the fifth number (525) of coins spent on proteins, and the sixth number (525) of coins spent on fats.

Statement 25. An embodiment of the invention includes the method according to statement 24, wherein:

converting (935), by the application (130) running on the system (105), the first percentage (445) of the total (410) number of coins spent on carbohydrates into the fourth number (525) of coins spent on carbohydrates includes rounding (950), by the application (130) running on the system (105), the fourth number (525) of coins spent on carbohydrates to a first nearest whole number;

converting (940), by the application (130) running on the system (105), the second percentage (445) of the total (410) number of coins spent on proteins into the fifth number (525) of coins spent on proteins includes rounding (955), by the application (130) running on the system (105), the fifth number (525) of coins spent on proteins to a second nearest whole number; and converting (945), by the application (130) running on the system (105), the third percentage (445) of the total (410) number of coins spent on fats into the sixth number (525) of coins spent on fats includes rounding (960), by the application (130) running on the system (105), the third number (525) of coins spent on fats to a sixth nearest whole number.

Statement 26. An embodiment of the invention includes the method according to statement 14, further comprising:
determining (1005), by the application (130) running on the system (105), a sodium intake in the serving (520) of the food (515) consumed by the user;
comparing (1010), by the application (130) running on the system (105), the sodium intake relative with a recommended sodium intake; and
presenting (1015), by the application (130) running on the system (105), to the user a comparison of the sodium intake relative to the recommended sodium intake.

Statement 27. An embodiment of the invention includes the method according to statement 14, further comprising:
determining (805), by the application (130) running on the system (105), an initial number (525) of coins for the user;
receiving (1105), by the application (130) running on the system (105), information from the user about an exercise (460) performed; and
increasing (1115), by the application (130) running on the system (105), the initial number (525) of coins for the user based at least in part on the exercise (460) performed.

Statement 28. An embodiment of the invention includes the method according to statement 27, wherein the exercise (460) performed is drawn from a set including walking, running, bicycling, and stair climbing.

Statement 29. An embodiment of the invention includes an article, comprising a non-transitory storage medium, the non-transitory storage medium having stored thereon instructions that, when executed by a system (105), result in:
identifying (705), in an application (130) running on the system (105), a serving (520) of a food (515) consumed by a user;
determining (710), by the application (130) running on the system (105), a first number (615) of grams of carbohydrates in the serving (520) of the food (515);
determining (715), by the application (130) running on the system (105), a second number (620) of grams of proteins in the serving (520) of the food (515);
determining (720), by the application (130) running on the system (105), a third number (625) of grams of fats in the serving (520) of the food (515); and
calculating (725), by the application (130) running on the system (105), a number (525) of coins for the serving (520) of the food (515) based at least in part on the first number (615) of grams of carbohydrates, the second number (620) of grams of proteins, and the third number (625) of grams of fats.

Statement 30. An embodiment of the invention includes the article according to statement 29, the non-transitory storage medium having stored thereon further instructions that, when executed by the system (105), result in storing (730) the number (525) of coins associated with the serving (520) of the food (515) in a table (505).

Statement 31. An embodiment of the invention includes the article according to statement 29, wherein:
determining (710), by the application (130) running on the system (105), the first number (615) of grams of carbohydrates in the serving (520) of the food (515) includes accessing (710), by the application (130) running on the system (105), the first number (615) of grams of carbohydrates in the serving (520) of the food (515) from a table (605);
determining (715), by the application (130) running on the system (105), the second number (620) of grams of proteins in the serving (520) of the food (515) includes accessing (715), by the application (130) running on the system (105), the second number (620) of grams of proteins in the serving (520) of the food (515) from the table (605); and
determining (720), by the application (130) running on the system (105), the third number (625) of grams of fats in the serving (520) of the food (515) includes accessing (720), by the application (130) running on the system (105), the third number (625) of grams of fats in the serving (520) of the food (515) from the table (605).

Statement 32. An embodiment of the invention includes the article according to statement 29, wherein:
determining (710), by the application (130) running on the system (105), the first number (615) of grams of carbohydrates in the serving (520) of the food (515) includes receiving (710), at the application (130) running on the system (105), the first number (615) of grams of carbohydrates in the serving (520) of the food (515) from the user;
determining (715), by the application (130) running on the system (105), the second number (620) of grams of proteins in the serving (520) of the food (515) includes receiving (715), at the application (130) running on the system (105), the second number (620) of grams of proteins in the serving (520) of the food (515) from the user; and
determining (720), by the application (130) running on the system (105), the third number (625) of grams of fats in the serving (520) of the food (515) includes receiving (720), at the application (130) running on the system (105), the third number (625) of grams of fats in the serving (520) of the food (515) from the user.

Statement 33. An embodiment of the invention includes the article according to statement 29, the non-transitory storage medium having stored thereon further instructions that, when executed by the system (105), result in:
determining (805) an initial number (525) of coins for the user;
receiving (830) an input from the user that the serving (520) of the food (515) has been consumed; and
deducting (840) the number (525) of coins from the initial number (525) of coins.

Statement 34. An embodiment of the invention includes the article according to statement 29, the non-transitory storage medium having stored thereon further instructions that, when executed by the system (105), result in:
determining (845) a total (410) number of coins spent by the user;
receiving (830) an input from the user that the serving (520) of the food (515) has been consumed; and
increasing (850) the total (410) number of coins spent by the user by the number (525) of coins.

Statement 35. An embodiment of the invention includes the article according to statement 29, the non-transitory storage medium having stored thereon further instructions that, when executed by the system (105), result in:
receiving (810), by the application (130) running on the system (105), from the user a request for information about the serving (520) of the food (515); and
presenting (820), by the application (130) running on the system (105), to the user the number (525) of coins associated with the serving (520) of the food (515).

Statement 36. An embodiment of the invention includes the article according to statement 29, the non-transitory storage medium having stored thereon further instructions that, when executed by the system (105), result in:
determining (910), by the application (130) running on the system (105), a list of servings (520) of foods (515) consumed by the user;
determining (915), by the application (130) running on the system (105), a total (410) number of coins spent by the user;
determining (920), by the application (130) running on the system (105), a first percentage (445) of the total (410) number of coins spent on carbohydrates;
determining (925), by the application (130) running on the system (105), a second percentage (445) of the total (410) number of coins spent on proteins; and
determining (930), by the application (130) running on the system (105), a third percentage (445) of the total (410) number of coins spent on fats.

Statement 37. An embodiment of the invention includes the article according to statement 36, the non-transitory storage medium having stored thereon further instructions that, when executed by the system (105), result in:
receiving (905), at the application (130) running on the system (105), from the user a request for macronutrient details; and
presenting (975), by the application (130) running on the system (105), to the user the first percentage (445) of the total (410) number of coins spent on carbohydrates, the second percentage (445) of the total (410) number of coins spent on proteins, and the third percentage (445) of the total (410) number of coins spent on fats.

Statement 38. An embodiment of the invention includes the article according to statement 36, the non-transitory storage medium having stored thereon further instructions that, when executed by the system (105), result in:
determining (980), by the application (130) running on the system (105), that the first percentage (445) of the total (410) number of coins spent on carbohydrates, the second percentage (445) of the total (410) number of coins spent on proteins, and the third percentage (445) of the total (410) number of coins spent on fats are not balanced; and
suggesting (985), by the application (130) running on the system (105), that the user consume a second serving (520) of a second food (515) to bring the first percentage (445) of the total (410) number of coins spent on carbohydrates, the second percentage (445) of the total (410) number of coins spent on proteins, and the third percentage (445) of the total (410) number of coins spent on fats into balance.

Statement 39. An embodiment of the invention includes the article according to statement 36, wherein presenting (820), by the application (130) running on the system (105), to the user the first percentage (445) of the total (410) number of coins spent on carbohydrates, the second percentage (445) of the total (410) number of coins spent on proteins, and the third percentage (445) of the total (410) number of coins spent on fats includes:
converting (935), by the application (130) running on the system (105), the first percentage (445) of the total (410) number of coins spent on carbohydrates into a fourth number (525) of coins spent on carbohydrates;
converting (940), by the application (130) running on the system (105), the second percentage (445) of the total (410) number of coins spent on proteins into a fifth number (525) of coins spent on proteins;
converting (945), by the application (130) running on the system (105), the third percentage (445) of the total (410) number of coins spent on fats into a sixth number (525) of coins spent on fats; and
presenting (975), by the application (130) running on the system (105), to the user the fourth number (525) of coins spent on carbohydrates, the fifth number (525) of coins spent on proteins, and the sixth number (525) of coins spent on fats.

Statement 40. An embodiment of the invention includes the article according to statement 39, wherein:
converting (935), by the application (130) running on the system (105), the first percentage (445) of the total (410) number of coins spent on carbohydrates into the fourth number (525) of coins spent on carbohydrates includes rounding (950), by the application (130) running on the system (105), the fourth number (525) of coins spent on carbohydrates to a first nearest whole number;
converting (940), by the application (130) running on the system (105), the second percentage (445) of the total (410) number of coins spent on proteins into the fifth number (525) of coins spent on proteins includes rounding (955), by the application (130) running on the system (105), the fifth number (525) of coins spent on proteins to a second nearest whole number; and
converting (945), by the application (130) running on the system (105), the third percentage (445) of the total (410) number of coins spent on fats into the sixth number (525) of coins spent on fats includes rounding (960), by the application (130) running on the system (105), the third number (525) of coins spent on fats to a sixth nearest whole number.

Statement 41. An embodiment of the invention includes the article according to statement 29, the non-transitory storage medium having stored thereon further instructions that, when executed by the system (105), result in:
determining (1005), by the application (130) running on the system (105), a sodium intake in the serving (520) of the food (515) consumed by the user;
comparing (1010), by the application (130) running on the system (105), the sodium intake relative with a recommended sodium intake; and
presenting (1015), by the application (130) running on the system (105), to the user a comparison of the sodium intake relative to the recommended sodium intake.

Statement 42. An embodiment of the invention includes the article according to statement 29, the non-transitory storage medium having stored thereon further instructions that, when executed by the system (105), result in:
determining (805), by the application (130) running on the system (105), an initial number (525) of coins for the user;
receiving (1105), by the application (130) running on the system (105), information from the user about an exercise (460) performed; and increasing (1115), by the application (130) running on the system (105), the initial number (525) of coins for the user based at least in part on the exercise (460) performed.

Statement 43. An embodiment of the invention includes the article according to statement 42, wherein the exercise (460) performed is drawn from a set including walking, running, bicycling, and stair climbing.

Consequently, in view of the wide variety of permutations to the embodiments described herein, this detailed description and accompanying material is intended to be illustrative only, and should not be taken as limiting the scope of the invention. What is claimed as the invention, therefore, is all such modifications as may come within the scope and spirit of the following claims and equivalents thereto.

What is claimed is:

1. A system, comprising:
    a processor;
    storage for a table of foods consumed by a user, the table associating a serving of food with a number of coins, wherein the servings of food are, via the processor, automatically populated into the table in response to audio input received, via a microphone, and recognized using speech recognition techniques, and wherein a date and a time for which the servings of food were consumed by the user are associated, via the processor, with the stored servings of food;
    a presentation system operative to inform the user that the user has spent too many coins based at least in part on a total of the number of coins in the table exceeding a recommended number of coins for the user, and wherein the presentation system displays the total of the number of coins in the table and the recommended number of coins to the user, concurrently; and
    a user interface to receive an exercise performed by the user,
    wherein the processor is operative to determine the exercise performed is part of a general fitness regimen;
    wherein the processor is operative to, in response to a determination the exercise performed is part of the general fitness regimen, maintain the initial number of coins,
    wherein the number of coins represents a portion of a daily calorie need of the user;
    wherein the processor is operative to calculate a first percentage of the total of the number of coins spent on carbohydrates, a second percentage of the total of the number of coins spent on proteins, and a third percentage of the total of the number of coins spent on fats;
    wherein the presentation system is operative to present the first percentage of the total of the number of coins spent on carbohydrates, the second percentage of the total of the number of coins spent on proteins, and the third percentage of the total of the number of coins spent on fats to the user;
    wherein the presentation system is further operative to suggest that the user consume a second serving of a second food to bring the first percentage of the total number of coins spent on carbohydrates, the second percentage of the total number of coins spend on proteins, and the third percentage of the total number of coins spent on fats into balance;
    wherein the presentation system is further operative to present, concurrently with the total of the number of coins in the table, the first percentage, the second percentage, and the third percentage as a number of coins rounded to a nearest whole number;
    wherein the processor predicts, based on the first and second servings of the first and second foods consumed by the user, a historical record of servings of food consumed by the user, the exercise performed by the user, a resting energy expenditure of the user, and a weekly weight loss goal of the user, the user will not achieve the weekly weight loss goal;
    wherein, in response to the prediction, the processor suggests, via the presentation system, one or more workouts to the user, based at least in part on the weekly weight loss goal, the resting energy expenditure of the user, an activity level of the user, an equipment preference of the user, and an activity preference of the user;
    wherein the one or more workouts include a set of repetitions and a set of sets of utilizing exercise bands, free weights, and exercise machines, respectively;
    wherein the one or more workouts further include a number of walked miles, a number of run miles, a number of cycled miles, and a number of stair climbing minutes;
    wherein the suggested one or more workouts are predicted, by the processor, to cause the user to achieve the weekly weight loss goal;
    determining by the processor, the user has completed the suggested one or more workouts; and
    increasing, by the processor, the resting energy expenditure of the user.

2. The system according to claim 1, further comprising a second table associating the serving of the food with the number of coins.

3. The system according to claim 2, wherein the second table further associates the serving of the food with a first number of grams of carbohydrates, a second number of grams of proteins, and a third number of grams of fats, wherein the first, second, and third numbers are tracked at least by an equivalent of tenths of the rounded whole number of coins presented to the user.

4. The system according to claim 1, wherein:
    the system further comprises the user interface to receive a request for information about the serving of food from the user; and
    the presentation system is operative to present the number of coins associated with the serving of food to the user.

5. The system according to claim 1, wherein:
    the processor is further operative to calculate a fourth number of coins spent on carbohydrates, a fifth number of coins spent on proteins, and a sixth number of coins spent on fats; and
    the presentation system is operative to present the fourth number of coins spent on carbohydrates, the fifth number of coins spent on proteins, and the sixth number of coins spent on fats to the user.

6. A method, comprising:
    identifying, in an application running on a system, a serving of a food consumed by a user, wherein the serving of food is, via the processor, automatically populated into a table in response to audio input received, via a microphone, and recognized using speech recognition techniques, and wherein a date and a time for which the serving of food was consumed by the user are associated, via the processor, with the stored serving of food;
    calculating, by the application running on the system, a number of coins for the serving of the food representing a portion of a daily calorie need of the user, and wherein a presentation system communicatively coupled to the system displays a total of the number of coins representing the daily calorie need of the user and the number of coins for the serving of food to the user, concurrently;

determining, by the application running on the system, an initial number of coins for the user;

receiving, by the application running on the system, information from the user about an exercise performed;

determine, by the application running on the system, the exercise performed is part of a general fitness regimen;

in response to the determination the exercise performed is part of the general fitness regimen, maintain, by the application running on the system, the initial number of coins for the user;

determining, by the application running on the system, a list of servings of foods consumed by the user;

determining, by the application running on the system, a total number of coins spent by the user;

determining, by the application running on the system, a first percentage of the total number of coins spent on carbohydrates;

determining, by the application running on the system, a second percentage of the total number of coins spent on proteins;

determining, by the application running on the system, a third percentage of the total number of coins spent on fats;

determining, by the application running on the system, that the first percentage of the total number of coins spent on carbohydrates, the second percentage of the total number of coins spent on proteins, and the third percentage of the total number of coins spent on fats are not balanced;

suggesting, by the application running on the system, that the user consume a second serving of a second food to bring the first percentage of the total number of coins spent on carbohydrates, the second percentage of the total number of coins spent on proteins, and the third percentage of the total number of coins spent on fats into balance;

predicting, based on the first and second servings of the first and second foods consumed by the user, a historical record of servings of food consumed by the user, the exercise performed by the user, a resting energy expenditure of the user, and a weekly weight loss goal of the user, the user will not achieve the weekly weight loss goal;

in response to the prediction, suggesting one or more workouts to the user, based at least in part on the weekly weight loss goal, the resting energy expenditure of the user, an activity level of the user, an equipment preference of the user, and an activity preference of the user;

wherein the one or more workouts include a set of repetitions and a set of sets of utilizing exercise bands, free weights, and exercise machines, respectively;

wherein the one or more workouts further include a number of walked miles, a number of run miles, a number of cycled miles, and a number of stair climbing minutes;

wherein the suggested one or more workouts are predicted to cause the user to achieve the weekly weight loss goal;

determining the user has completed the suggested one or more workouts; and increasing the resting energy expenditure of the user.

7. The method according to claim 6, further comprising storing the number of coins associated with the serving of food in the table.

8. The method according to claim 7, further comprising:
accessing, by the application running on the system, a first number of grams of carbohydrates in the serving of the food from the table;
accessing, by the application running on the system, a second number of grams of proteins in the serving of the food from the table; and
accessing, by the application running on the system, a third number of grams of fats in the serving of the food from the table, wherein the first, second, and third numbers are tracked at least by an equivalent of tenths of a rounded whole number of coins presented to the user.

9. The method according to claim 6, further comprising:
receiving an input from the user that the serving of the food has been consumed; and
increasing the total number of coins spent by the user by the number of coins.

10. The method according to claim 6, further comprising:
receiving, at the application running on the system, from the user a request for macronutrient details; and
presenting, by the application running on the system, to the user the first percentage of the total number of coins spent on carbohydrates, the second percentage of the total number of coins spent on proteins, and the third percentage of the total number of coins spent on fats.

11. The method according to claim 6, wherein presenting, by the application running on the system, to the user the first percentage of the total number of coins spent on carbohydrates, the second percentage of the total number of coins spent on proteins, and the third percentage of the total number of coins spent on fats includes:
converting, by the application running on the system, the first percentage of the total number of coins spent on carbohydrates into a fourth number of coins spent on carbohydrates;
converting, by the application running on the system, the second percentage of the total number of coins spent on proteins into a fifth number of coins spent on proteins;
converting, by the application running on the system, the third percentage of the total number of coins spent on fats into a sixth number of coins spent on fats; and
presenting, by the application running on the system, to the user the fourth number of coins spent on carbohydrates, the fifth number of coins spent on proteins, and the sixth number of coins spent on fats.

12. The method according to claim 11, wherein:
converting, by the application running on the system, the first percentage of the total number of coins spent on carbohydrates into the fourth number of coins spent on carbohydrates includes rounding, by the application running on the system, the fourth number of coins spent on carbohydrates to a first nearest whole number;
converting, by the application running on the system, the second percentage of the total number of coins spent on proteins into the fifth number of coins spent on protein includes rounding, by the application running on the system, the fifth number of coins spent on proteins to a second nearest whole number; and
converting, by the application running on the system, the third percentage of the total number of coins spent on fats into the sixth number of coins spent on fats includes rounding, by the application running on the system, the third number of coins spent on fats to a sixth nearest whole number.

13. An article, comprising a non-transitory storage medium, the non-transitory storage medium having stored thereon instructions that, when executed by a system, results in:

identifying, in an application running on the system, a serving of a food consumed by a user, wherein the serving of food is, via a processor, automatically populated into a table in response to audio input received, via a microphone, and recognized using speech recognition techniques, and wherein a date and a time for which the serving of food was consumed by the user are associated, via the processor, with the stored serving of food;

calculating, by the application running on the system, a number of coins for the serving of the food representing a portion of a daily calorie need of the user, and wherein a presentation system communicatively coupled to the system displays a total of the number of coins representing the daily calorie need of the user and the number of coins for the serving of food to the user, concurrently;

determining, by the application running on the system, an initial number of coins for the user;

receiving, by the application running on the system, information from the user about an exercise performed;

determine, by the application running on the system, the exercise performed is part of a general fitness regimen;

in response to the determination the exercise performed is part of the general fitness regimen, maintaining, by the application running on the system, the initial number of coins for the user;

determining, by the application running on the system, a list of servings of foods consumed by the user;

determining, by the application running on the system, a total number of coins spent by the user, wherein the total number of coins is tracked at least by an equivalent of tenths of a rounded whole number of coins presented to the user via the presentation system;

determining, by the application running on the system, a first percentage of the total number of coins spent on carbohydrates;

determining, by the application running on the system, a second percentage of the total number of coins spent on proteins;

determining, by the application running on the system, a third percentage of the total number of coins spent on fats;

determining, by the application running on the system, that the first percentage of the total number of coins spent on carbohydrates, the second percentage of the total number of coins spent on proteins, and the third percentage of the total number of coins spent on fats are not balanced;

suggesting, by the application running on the system, that the user consume a second serving of a second food to bring the first percentage of the total number of coins spent on carbohydrates, the second percentage of the total number of coins spent on proteins, and the third percentage of the total number of coins spent on fats into balance;

predicting, by the application running on the system, based on the first and second servings of the first and second foods consumed by the user, a historical record of servings of food consumed by the user, the exercise performed by the user, a resting energy expenditure of the user, and a weekly weight loss goal of the user, the user will not achieve the weekly weight loss goal:

in response to the prediction, suggesting by the application running on the system, one or more workouts to the user, based at least in part on the weekly weight loss goal, the resting energy expenditure of the user, an activity level of the user, an equipment preference of the user, and an activity preference of the user;

wherein the one or more workouts include a set of repetitions and a set of sets of utilizing exercise bands, free weights, and exercise machines, respectively;

wherein the one or more workouts further include a number of walked miles, a number of run miles, a number of cycled miles, and a number of stair climbing minutes;

wherein the suggested one or more workouts are predicted to cause the user to achieve the weekly weight loss goal;

determining by the application running on the system, the user has completed the suggested one or more workouts; and increasing, by the application running on the system, the resting energy expenditure of the user.

14. The article of claim 13, wherein determining the resting energy expenditure for the user includes variables representing at least a height, a weight, or an age of the user.

15. The article of claim 14, wherein calculating the daily calorie need of the user includes, at least in part:

determining a mathematical product of the resting energy expenditure of the user and an activity level factor of the user.

16. The article of claim 15, wherein the one or more workout suggestions are altered, based on user feedback.

17. The article of claim 13, wherein the second food is determined, based at least in part on an amount of sodium the user has consumed.

18. The article of claim 17, wherein the one or more suggested workouts is based on a target muscle.

19. The article of claim 17, wherein the one or more suggested workouts is based on a target muscle group.

20. The article of claim 19, wherein the one or more suggested workouts further includes a suggested warmup and a suggested warmdown.

* * * * *